United States Patent [19]
Hossack et al.

[11] Patent Number: 6,083,168
[45] Date of Patent: *Jul. 4, 2000

[54] ULTRASOUND IMAGING SYSTEM AND METHOD FOR IMPROVING RESOLUTION AND OPERATION

[75] Inventors: John A. Hossack, Palo Alto; John S. Wang, Sunnyvale, both of Calif.

[73] Assignee: Acuson Corporation, Mountain View, Calif.

[*] Notice: This patent is subject to a terminal disclaimer.

[21] Appl. No.: 09/244,819

[22] Filed: Feb. 4, 1999

Related U.S. Application Data

[63] Continuation of application No. 08/916,358, Aug. 22, 1997, Pat. No. 5,878,830.

[51] Int. Cl.⁷ .................................................... A61B 8/00
[52] U.S. Cl. ............................................................ 600/443
[58] Field of Search ................................... 600/443, 447; 128/916; 392/81; 73/626; 382/128, 293, 294, 295

[56] References Cited

U.S. PATENT DOCUMENTS

| | | |
|---|---|---|
| 3,640,271 | 2/1972 | Horton . |
| 4,580,219 | 4/1986 | Pelc et al. . |
| 4,581,636 | 4/1986 | Blaker et al. . |
| 4,712,037 | 12/1987 | Verbeek et al. . |
| 4,785,818 | 11/1988 | Hardin . |
| 4,945,767 | 8/1990 | Shirasaka . |
| 5,014,710 | 5/1991 | Maslak et al. . |
| 5,016,641 | 5/1991 | Schwartz . |
| 5,111,823 | 5/1992 | Cohen . |
| 5,115,809 | 5/1992 | Saitoh et al. . |
| 5,127,409 | 7/1992 | Daigle ..................................... 600/443 |
| 5,135,000 | 8/1992 | Akselrod et al. . |
| 5,165,414 | 11/1992 | Larson, III . |
| 5,195,520 | 3/1993 | Schlief et al. . |
| 5,197,477 | 3/1993 | Peterson et al. . |
| 5,215,093 | 6/1993 | Miyazaki et al. . |

(List continued on next page.)

FOREIGN PATENT DOCUMENTS

| | | |
|---|---|---|
| 0 357 164 | of 0000 | European Pat. Off. . |
| 0 770 352 A1 | 5/1997 | European Pat. Off. . |

OTHER PUBLICATIONS

"A Locally Quadratic Model of the Motion Estimation Error Criterion Function and Its Application to Subpixel Interpolations", Xiaoming Li and Cesar Gonzales, *IEEE Transactions On Circuits And Systems For Video Technology*, vol. 6, No. 1, Feb. 1996, pp. 118–122.

(List continued on next page.)

*Primary Examiner*—Francis J. Jaworski
*Attorney, Agent, or Firm*—Brinks Hofer Gilson & Lione

[57] ABSTRACT

An ultrasound system and method are provided for improving resolution and operation. The system applies different imaging parameters within and outside a region of interest in an ultrasound image to improve spatial and/or temporal resolution inside a region of interest. The system also increases an apparent frame rate within a region of interest in an ultrasound-image frame by generating a motion-compensated interpolated image based on measured motion. The ultrasound imaging system also performs a method for automatically adjusting ultrasound imaging parameters in at least a portion of an ultrasound image in response to transducer or image motion to improve spatial or temporal resolution. With the measured motion, the system can also alter an operating mode of an ultrasound transducer array in response to an absence of transducer motion. Further, the system corrects distortion in an acquired ultrasound image caused by transducer or image motion.

28 Claims, 9 Drawing Sheets

U.S. PATENT DOCUMENTS

| | | |
|---|---|---|
| 5,233,994 | 8/1993 | Shmulewitz . |
| 5,255,683 | 10/1993 | Monaghan . |
| 5,279,301 | 1/1994 | Tsukaya et al. . |
| 5,285,788 | 2/1994 | Arenson et al. . |
| 5,287,753 | 2/1994 | Routh et al. . |
| 5,313,948 | 5/1994 | Murashita et al. . |
| 5,358,466 | 10/1994 | Aida et al. . |
| 5,386,830 | 2/1995 | Powers et al. . |
| 5,390,674 | 2/1995 | Robinson et al. ........................ 600/443 |
| 5,396,285 | 3/1995 | Hedberg et al. . |
| 5,409,688 | 4/1995 | Quay . |
| 5,410,205 | 4/1995 | Gururaja . |
| 5,410,516 | 4/1995 | Uhlendorf et al. . |
| 5,417,213 | 5/1995 | Prince . |
| 5,417,214 | 5/1995 | Roberts et al. . |
| 5,425,366 | 6/1995 | Reinhardt et al. . |
| 5,433,204 | 7/1995 | Olson . |
| 5,433,207 | 7/1995 | Pretlow, III . |
| 5,438,554 | 8/1995 | Seyed-Bolorforosh et al. . |
| 5,443,071 | 8/1995 | Banjanin et al. . |
| 5,456,255 | 10/1995 | Abe et al. . |
| 5,456,257 | 10/1995 | Johnson et al. . |
| 5,469,849 | 11/1995 | Sasaki et al. . |
| 5,471,990 | 12/1995 | Thirsk . |
| 5,476,096 | 12/1995 | Olstad et al. ............................ 600/443 |
| 5,479,926 | 1/1996 | Ustuner et al. . |
| 5,482,046 | 1/1996 | Deitrich . |
| 5,503,153 | 4/1996 | Liu et al. . |
| 5,526,816 | 6/1996 | Arditi . |
| 5,531,224 | 7/1996 | Ellis et al. ........................... 600/443 X |
| 5,538,004 | 7/1996 | Bamber ................................... 600/443 |
| 5,540,909 | 7/1996 | Schutt . |
| 5,548,561 | 8/1996 | Hussain et al. . |
| 5,558,092 | 9/1996 | Unger et al. . |
| 5,560,364 | 10/1996 | Porter . |
| 5,565,921 | 10/1996 | Sasaki et al. . |
| 5,566,674 | 10/1996 | Weng ...................................... 600/443 |
| 5,577,505 | 11/1996 | Brock-Fisher et al. . |
| 5,579,768 | 12/1996 | Klesenski . |
| 5,579,770 | 12/1996 | Finger . |
| 5,582,173 | 12/1996 | Li .......................................... 600/443 |
| 5,588,435 | 12/1996 | Weng et al. . |
| 5,601,085 | 2/1997 | Ostensen et al. . |
| 5,601,086 | 2/1997 | Pretlow, III et al. . |
| 5,608,690 | 3/1997 | Hossack et al. . |
| 5,617,862 | 4/1997 | Cole et al. . |
| 5,628,322 | 5/1997 | Mine . |
| 5,632,277 | 5/1997 | Chapman et al. . |
| 5,654,509 | 8/1997 | Miele et al. . |
| 5,667,373 | 9/1997 | Wright et al. . |
| 5,699,806 | 12/1997 | Weff et al. ............................. 600/454 |
| 5,718,228 | 2/1998 | Hiruta et al. . |
| 5,724,976 | 3/1998 | Mine et al. . |
| 5,734,738 | 3/1998 | Sato ....................................... 382/128 |
| 5,776,066 | 7/1998 | Noch et al. ............................. 600/443 |
| 5,782,766 | 7/1998 | Wang et al. ............................ 600/443 |
| 5,873,830 | 2/1999 | Hossach et al. ........................ 600/447 |
| 5,876,342 | 3/1999 | Chen et al. ............................. 600/443 |
| 5,885,218 | 3/1999 | Teo et al. ............................... 600/443 |
| 5,910,114 | 6/1999 | Noch et al. ............................. 600/437 |
| 5,946,425 | 8/1999 | Bore, Jr. et al. ........................ 382/294 |

OTHER PUBLICATIONS

"A Novel Method for Angle Independent Ultrasonic Imaging of Blood Flow and Tissue Motion", Laurence N. Bohs and Gregg E. Trahey, *IEEE Transactions On Biomedical Engineering*, vol. 38, No. 3, Mar. 1991, pp. 280–286.

B. Schrope, et al., "Simulated Capillary Blood Flow Measurement Using A Nonlinear Ultrasonic Contrast Agent," Ultrasonic Imaging 14 (1992).

Chandra M. Sehgal, PhD., et al., "Sonographic Enhancement of Renal Cortex by Contrast Media." J. Ultrasound Med, 14; pp. 741–748 (1995).

Chandra M. Sehgal, PhD., et al., "Influence of Postprocessing Curves on Contrast–Echographic Imaging: Preliminary Studies" J. Ultrasound Med, 14; pp. 735–740 (1995).

Chiang C. Mei, et al., "Parametric resonance of a spherical bubble." J. Fluid Mech. (1991) vol. 229.

Deborah J. Rubens, M.D., "Sonoelasticity Imaging of Prostate Cancer: In Vitro Results." Radiology, vol. 195, No. 2, 1995.

Eric J. Chen, et al., "Young's Modulus Measurements of Soft Tissues with Application to Elasticity Imaging." IEEE Transactions on Ultrasonics, Ferroelectrics, and Frequency Control, vol. 43, No. 1, Jan. 1996.

Fred Lee, Jr., M.D., "Sonoelasticity Imaging: Results in in Vitro Tissue Specimens." Radiology, vol. 181, No. 1, Oct. 1991.

H. Edward Karrer, et al., "A Phased Array Acoustic Imaging System for Medical Use." 1980 Ultrasonics Symposium.

"HP Ultrasound Technologies—Viability." About HP Ultrasound Imaging, WWW document 1997.

*Image Sequence Analysis,* T.S. Huang, Springer Series in Information Sciences, New York 1981, vol. 5, pp. 229–309.

"Interframe Interpolation of Cinematic Sequences", J. Ribas–Corbera and J. Sklansky, *Journal Of Visual Communication And Image Representation,* vol. 4, No. 4, Dec. 1993, pp. 392–406.

J. Ophir, et al., "Elastography: A Quantitative Method for Imaging the Elasticity of Biological Tissues." Ultrasonic Imaging 13, (1991).

J. W. Norris, "The non–linear oscillation of radially symmetric bubble in a time periodic pressure field." Dynamics and Stability of Systems, vol. 9, No. 1 (1994).

J.A. Hossack, et al., "Improving transducer performance using multiple active layers." SPIE vol. 1733 (1992).

Janet B. Jones–Oliveira, et al., "Transient fluid—solid interaction of submerged spherical shells revisited: Proliferation of frequencies and acoustic radiation effects." Acoustical Society of America, 96(2) Pt. 1, Aug. 1994.

John A. Hossack, et al., "Improving the Characteristics of a Transducer Using Multiple Piezoelectric Layers." IEEE Transactions on Ultrasonics, Ferroelectrics, and Frequency Control, vol. 40, No. 2, Mar. 1993.

K.J. Parker, et al., "Tissue Response to Mechanical Vibrations for 'Sonoelasticity Imaging'." Ultrasound in Med. & Biol., vol. 16, No. 3, (1990).

Ken Ishihara et al., "New Approach to Noninvasive Manometry Based on Pressure Dependent Resonant Shift of Elastic Microcapsules in Ultrasonic Frequency Characteristics." Japanese J. of Applied Physics, vol. 2 (1988).

Kevin J. Parker, PhD, et al., "Sonoelasticity of Organs: Shear Waves Ring a Bell." J. Ultrasound Med. 11 (1992).

Kotaro Sato, et al., "Numerical analysis of a gas bubble near a rigid boundary in an oscillatory pressure field." J. Acoustical Society of America, 95(5), May 1994.

L.W. Anson et al., "Ultrasonic scattering from spherical shells including viscous and thermal effects." J. Acoustical Society of America, 93(4), Apr. 1993.

Marc Gensane, "Bubble population measurements with a parametric array." 1994 Acoustical Society of America, 95 (6) Jun.

Michael S. Longuet–Higgins, Resonance in nonlinear bubble oscillations. J. Fluid Mech. (1991) vol. 224.

Michalakis A. Averkiou, et al., "Self–demodulation of amplitude–and frequency–modulated pulses in a thermoviscous fluid." J. Acoustical Society of America, 94 (5), Nov. 1993.

Nico de Jong, "Physical properties and technical aspects of ultrasound contrast agents."

Pi Hsien Chang, et al., "Second Harmonic Imaging and Harmonic Doppler Measurements with Albunex." IEEE Transactions on Ultrasonics, Ferroelectrics, and Frequency Control, vol. 42, No. 6, Nov. 1996.

"Restoration of the Velocity Field of the Heart from Two–Dimensional Echocardiograms", Guy E. Mailloux, Francis Langlois, Patrice Y. Simard, and Michel Bertrand, *IEEE Transactions On Medical Imaging,* vol. 8, No. 2, Jun. 1989, pp. 143–153.

Robert M. Lerner, et al., "'Sonoelasticity' Images Derived from Ultrasound Signals in Mechanically Vibrated Tissues." Ultrasound in Med. and Biol., vol. 16, No. 3, 1990.

Sharon L. Mulvagh, M.D., et al., "Abstract Session IV Contrast and Ischemia." Journal of the American Society of Echocardiography, vol. 8, No. 3, May 1995.

Shmuel Gottlieb, M.D. et al., "Effect of Pressure on Echocardiographic Videodensity from Sonicated Albumin: An In Vitro Model." J. Ultrasound Med. 14 (1995).

"Supplement to Journal of the American College of Cardiology." American College of Cardiology, 45$^{th}$ Annual Scientific Session, Mar. 24–27, 1996 pp. 21A, 63A, 239–240A.

T.G. Leighton, "Transient excitation of isonated bubbles." Research Notes.

Ted Christopher, "Finite Amplitude Distortion–Based Inhomogeneous Pulse Echo Ultrasonic Imaging." IEEE Transactions on Ultrasonics, Ferroelectrics, and Frequency Control, vol. 44, No. 1, Jan. 1997.

V.L. Newhouse et al., "Bubble size measurements using the nonlinear mixing of two frequencies." J. Acoust. Soc. Am. 75 (5), May 1984.

Vokmar Uhlendorf, et al., "Nonlinear Acoustical Response of Coated Microbubbles in Diagnostic Ultrasound." IEEE 1994 Ultrasonics Symposium.

William Armstrong, M.D., et al., "American Society of Echocardiography Position Paper on Contrast Echocardiography." draft 1—Jun. 6, 1994.

Yang–Sub Lee, et al., "Time–domain modeling of pulsed finite–amplitude sound beams." J. Acoustical Society of America, 97 (2), Feb. 1995.

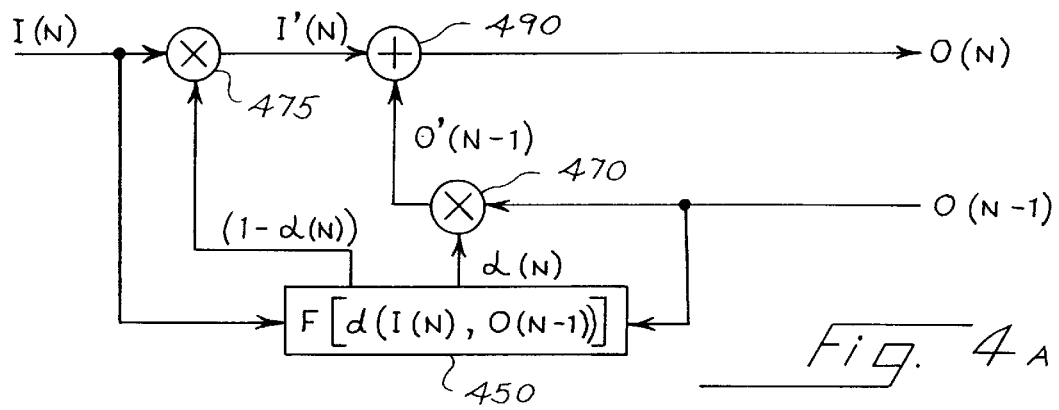
Fig. 4A
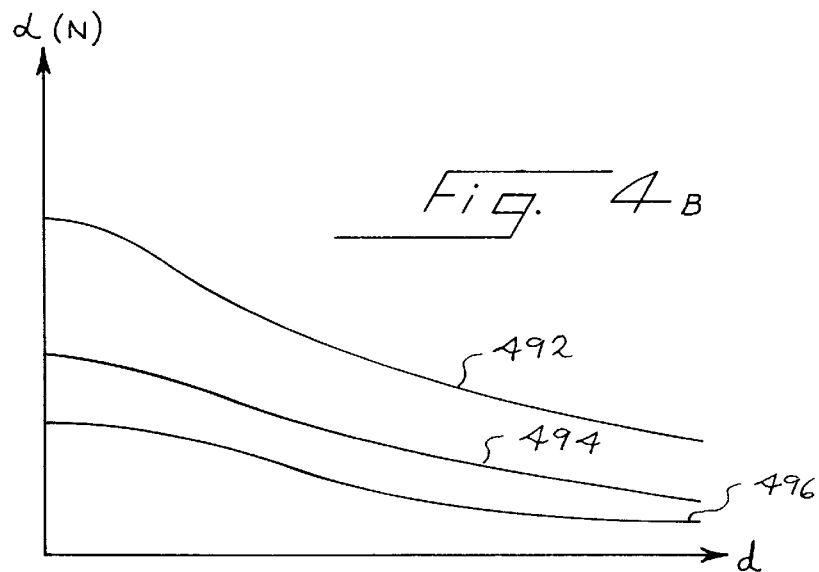
Fig. 4B
Fig. 5
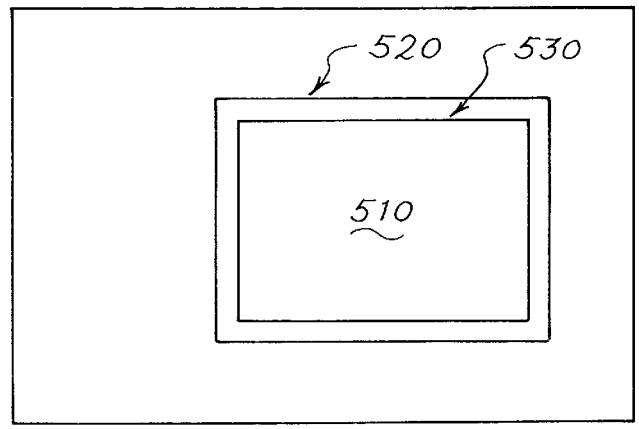

ULTRASOUND IMAGING SYSTEM AND METHOD FOR IMPROVING RESOLUTION AND OPERATION

This application is a continuation of U.S. application Ser. No. 08/916,358, filed Aug. 22, 1997, which is now U.S. Pat. No. 5,873,830.

BACKGROUND OF THE INVENTION

There are several limitations of conventional ultrasound imaging systems that result in reduced spatial and temporal resolution in generated ultrasound images. One limitation is that conventional systems do not offer much flexibility in controlling imaging parameters on an intra-frame or regional basis. For example, many imaging parameters such as filtering, operating frequency, gain, number of transmit foci, and line density are uniform across the image frame, although line density may follow a predetermined reduction toward the sides of the image. Other imaging parameters may be controlled on a regional basis in a very limited manner. For example, gain in the axial or the lateral imaging dimension can be controlled in a region by using slide potentiometers for each depth in the image. The Regional Expansion® feature and the zoom feature found in commercial imaging systems also provide a very limited amount of regional control. The Regional Expansion® feature increases line density within a region to enhance spatial resolution, but the area outside the region is not scanned. The zoom feature merely magnifies a region, typically to fill the display screen. Additionally, modes such as color flow velocity, energy, or combined energy and velocity modes with a B-mode display can operate in a particular region of the image.

Another limitation of conventional ultrasound imaging systems is that they typically suffer from low frame rates. Because ultrasound systems typically present one image for every set of lines acquired, there is a tradeoff between spatial resolution and frame rate. That is, if a system is performing deep, detailed imaging requiring, for example, high line density and multiple transmit foci, a greater amount of time is required to acquire a set of lines. This increased amount of time can result in a frame rate that will be uselessly low. For example, with 256 lines, an imaging depth of 300 mm, and 5 transmit focal zones, the frame rate is merely two frames per second. In many areas (such as cardiology), a severely compromised frame rate is unacceptable. While repeatedly displaying the generated frames can match the video refresh rate (30 frames per second in the United States), repeated frames provide no new information to the user.

A third limitation of conventional ultrasound imaging systems is due to the complexity of spatial and temporal controls. Typically, a user quickly scans a patient to find a particular area of interest and then slowly scans that area to acquire a detailed image. Although the optimal imaging parameters are different in a fast scan than in a slow scan, many users choose not to fully optimize these parameters because adjusting imaging controls is often cumbersome.

A fourth limitation concerns transducer overheating. With some imaging modes, such as Color Doppler, the transducer will reach an elevated temperature if, while the ultrasound system is powered, the transducer is not used for imaging. Elevated temperatures can be damaging to the transducer and have been implicated as a contributing factor to reduced probe life. Elevated temperatures are also undesirable to a patient if a hot probe is applied to the patient. Some approaches to solving this problem include attaching a magnetic position sensor or an accelerometer to the transducer probe to automatically turn off the probe when no motion is sensed—an indication that the probe is not in use. These sensors are typically expensive (partly because they offer more features than are needed to solve the problem) and require modifications to be made to the probe. Other methods involve using latched probe holders, but to be effective, these methods require the user to place the probe in the proper holder. There is, therefore, a need for an inexpensive alternative that does not require user intervention.

A fifth limitation of conventional ultrasound imaging systems is that the displayed image typically exhibits geometric distortions due to image or transducer motion during the acquisition of an image frame. Scan lines in an ultrasound frame are acquired sequentially—not simultaneously. Accordingly, a finite amount of time elapses between the acquisition of the left-most line and the right-most line in an image frame. Image or transducer motion after the ultrasound system acquires the left-most line but before it acquires the right-most line can result in a distorted image. Distortions can also be caused by high transmit focus zone formats and in the mixed B-mode/Color Flow modes where there is a significant time delay between B-Mode lines acquired on the left and right hand side of the color box. An additional distortion occurs when transducer motion results in a scan line being fired at a physical location that corresponds to a location outside the image frame.

There is, therefore, a need for an ultrasound system and method that will overcome the problems described above.

SUMMARY OF THE INVENTION

The present invention is directed to an ultrasound system and method for improving resolution and operation. According to a first aspect of this invention, an ultrasound imaging system performs a method for improving spatial characteristics within a region of interest within an ultrasound image. The method comprises the steps of selecting a region of interest in an ultrasound image; selectively applying a first set of imaging parameters inside the region of interest to improve spatial resolution inside the region of interest, said first set being different from a second set of imaging parameters applied outside the region of interest; and assembling a composite image comprising a first image portion within the region of interest and a second image portion outside the region of interest, said first and second image portions being in the same imaging mode.

Imaging parameters that can be selectively applied comprise one or more of the following: (a) line density, (b) transmit foci per scan line, (c) pre-detection filter characteristics, (d) post-detection filter characteristics, (e) post-processing map characteristics, (f) ultrasound operating frequency, (g) transmit power, (h) logarithmic compression profiles, (i) multiple receive lines per transmit line, (j) transmit pulse shape, and (k) receive frequency band.

According to a second aspect of this invention, an ultrasound imaging system performs a method for improving temporal characteristics within a region of interest within an ultrasound image. The method comprises the steps of selecting a region of interest of an ultrasound-image frame; selectively applying a first set of imaging parameters inside the region of interest to improve temporal resolution inside the region of interest, said first set being different from a second set of imaging parameters applied outside the region of interest; and assembling a composite image comprising a first image portion within the region of interest and a second image portion outside the region of interest, said first and second image portions being in the same imaging mode.

Temporal resolution can be improved, for example, by increasing an actual frame rate inside the region of interest by acquiring additional real ultrasound-image frames inside the region of interest. Motion-compensated interframe interpolation can match the frame rate of the areas inside and outside the region of interest by measuring motion between a first and a second ultrasound-image frame outside of the region of interest and generating a motion-compensated interpolated frame. Alternatively, a real ultrasound-image frame can be generated outside the region of interest if an accurate measure of motion cannot be made.

Another way in which temporal resolution can be improved is by using a different persistence level inside the region of interest than outside the region of interest. Persistence can be varied as a function of measured motion within the region of interest.

Yet another way in which temporal characteristics can be varied is by increasing an apparent frame rate of an ultrasound imaging system. To accomplish this, the imaging system can perform a method comprising the steps of manually or automatically selecting a region of interest of an ultrasound image, measuring motion between a first and second ultrasound-image frame in a region of interest, generating a motion-compensated interpolated image inside the region of interest based on the measured motion, and then inserting the motion-compensated interpolated image between the first and second ultrasound-image frames inside the region of interest.

According to a third aspect of this invention, a method for automatically adjusting ultrasound imaging parameters in an ultrasound-image frame in response to transducer or image motion comprises the steps of measuring motion and then automatically applying imaging parameters in a region of interest in an ultrasound image in response to measured motion. Motion can be measured by a motion sensor in a transducer or by measuring motion of a sub-block of pixels between at least two ultrasound-image frames. Imaging parameters in the region of interest can be automatically applied to improve spatial or temporal resolution in response to measured motion being below or above a threshold value, respectively.

According to a fourth aspect of this invention, a method is provided for automatically altering an operating mode of an ultrasound transducer array in response to an absence of transducer motion to reduce the risk of transducer heating. This method comprises the steps of measuring motion of a transducer array by measuring motion of a sub-block of pixels between at least two ultrasound-image frames and automatically altering an operating mode of a transducer array in response to an absence of measured motion. To alter the operating mode in response to an absence of measured motion, an ultrasound system can remove or reduce power applied to the transducer array or disable imaging modes that cause elevated temperatures in the transducer array.

According to a fifth aspect of this invention, a method for correcting distortion caused by transducer or image motion in a region of interest in an ultrasound-image frame comprises the steps of measuring motion and automatically generating a distortion-corrected image inside a region of interest in response to the measured motion. Motion can be measured by a motion sensor in a transducer or by measuring motion of a sub-block of pixels between at least two ultrasound-image frames. A distortion-corrected image can be generated by estimating an effect of the measured motion on line spacing and reprocessing line data with corrected line spacing. A distortion-corrected image can also be generated by repositioning sub-blocks of pixels in response to motion.

BRIEF DESCRIPTION OF THE DRAWINGS

FIG. 4A shows an operational block diagram for creating an output image frame using a persistence filter coefficient in a selected region of interest.

FIG. 4B is a graph which illustrates characteristics of three different filter designs which can be used to generate a persistence filter coefficient.

FIG. 5 illustrates a technique for spatially smoothing a composite image.

DETAILED DESCRIPTION OF THE PRESENTLY PREFERRED EMBODIMENTS

COMPOSITE IMAGE EMBODIMENTS

Figure 1:
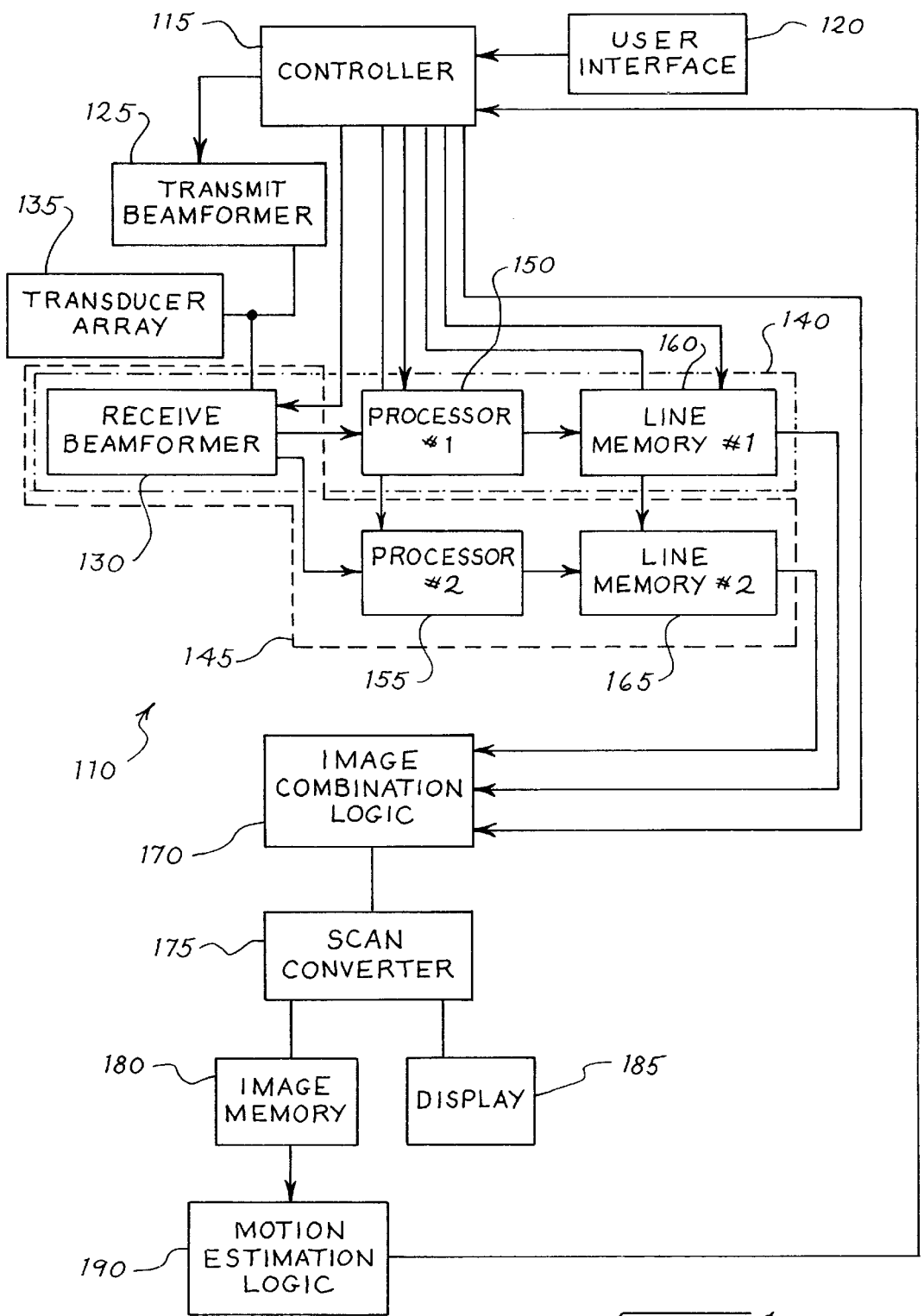
FIG. 1 is a block diagram of an ultrasound imaging system of a preferred embodiment.

Turning now to the figures, FIG. 1 shows a block diagram of an ultrasound imaging system 110. The ultrasonic imaging system 110 includes a controller 115 with a user interface 120. The controller 115 is coupled to a transmit beamformer 125, which is coupled to a transducer array 135. As used herein, "coupled to" means directly coupled to or indirectly coupled through one or more components. Similarly, "responsive to" means directly responsive to or indirectly responsive through one or more components.

This system 110 further comprises a first and second signal path 140, 145, comprising a first and second processor 150, 155, a first and second line memory 160, 165, and a receive beamformer 130. While FIG. 1 shows the first and second signal paths 140, 145 sharing one beamformer 130, it is important to note that each signal path can contain its own receive beamformer. The first and second signal paths 140, 145 are responsive to the transducer array 135 and are coupled to image combination logic 170. The image combination logic 170 is coupled to a scan converter 175, which is coupled to an image memory 180 and a display 185. Motion estimation logic 190 is responsive to the image memory 180 and is coupled to the controller 115, which is coupled to each component of the system 110.

As with conventional ultrasound systems, this system 110 performs ultrasonic visualization, the well-known interrogating-and-imaging process which includes ultrasound generation, ultrasound detection, image reconstruction, and image presentation phases. During the ultrasound generation phase, the transmit beamformer 125 applies multiple signals to elements of a transducer array 135 to cause the elements to vibrate and emit ultrasonic energy to a tissue. Next, in the ultrasound detection phase, the receive beamformer 130 measures the signals created by the transducer array 135 when ultrasonic energy reflected by the structures in the tissue impinge on the transducer array 135.

The signals generated by the receive beamformer 130 are channeled to the scan converter 175 for image reconstruction. During this phase, the scan converter 175 processes the detected signals to create an image, which is presented on the display 185 during the image presentation phase. Additionally, the image can be stored in the image memory 180.

The controller 115 controls the operation of the components of the system 110. A user, via the user interface 120, can adjust imaging parameters such as, but not limited to, image depth, image width, and frame rate. The controller 115 interprets the set-up information entered by the user and configures the components of the system 110 accordingly. Alternatively, the controller 115 can establish imaging parameters without input from the user.

Unlike conventional ultrasound systems, this system 110 comprises two signal paths 140, 145 and motion estimation logic 190. With these components and appropriate programming in the controller 115, this system 110 comprises means for selecting a region of interest within an ultrasound-image frame; means for selectively applying a first set of imaging parameters inside the region of interest, said first set being different from a second set of imaging parameters applied outside the region of interest; and image assembly means for assembling a composite image comprising a first image portion within the region of interest and a second image portion outside the region of interest, said first and second image portions being in the same imaging mode. As used herein, "set" includes one and more than one member.

Figure 2:
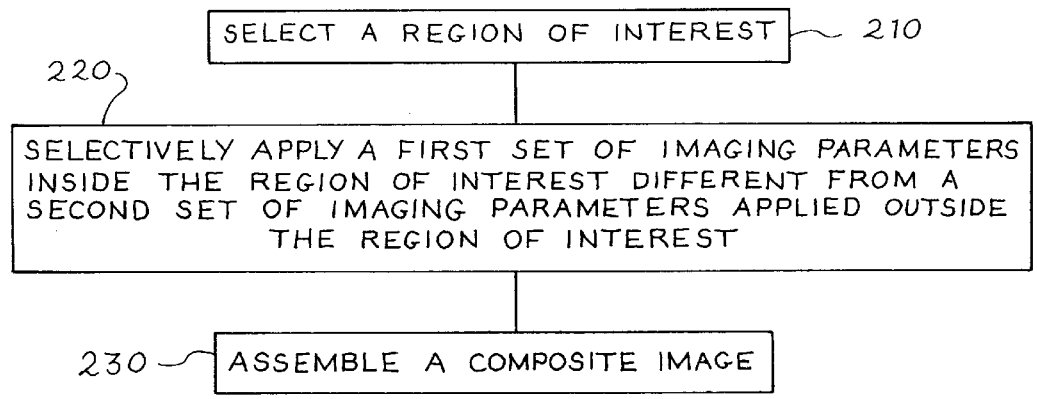
FIG. 2 is a flow chart of a method for forming an enhanced image within an ultrasound-image frame.

FIG. 2 is a flow chart illustrating a method for improving spatial characteristics within a region of interest in an ultrasound image. First, a region of interest in an ultrasound image is selected (step 210). Next, the system selectively applies a first set of imaging parameters inside the region of interest to improve spatial and/or temporal resolution inside the region of interest, said first set being different from a second set of imaging parameters applied outside the region of interest (step 220). Then, a composite image comprising a first image portion within the region of interest and a second image portion outside the region of interest is assembled (step 230). Both image portions can be in the same imaging mode (e.g., both image portions can be B-mode images, both can be color Doppler images, and so forth). The steps of this method, which will be described in more detail below, can be performed in real time.

Selecting a Region of Interest

The first step (step 210) of this method is to select a region of interest in an ultrasound image. The region of interest can comprise the entire ultrasound image or a portion thereof and covers a selected set of scan lines and at least a portion of range direction for the selected set of scan lines. The region of interest can be rectangular for a linear format and arc-shaped for a sector/Vector® format.

A user can manually select the region of interest though the user interface 120. For example, a user can use a track ball to position graphical lines on the display 185 to mark the region of interest around a detailed and fast moving object, such as a heart valve leaflet. The user can also use an "Image Width" function found in some commercially available ultrasound imaging systems to designate the region of interest.

Alternatively, the region of interest can be automatically selected (e.g., by the controller 115) to surround regions of motion. For example, motion estimation logic 190 performing an image motion tracking technique can determine frame-to-frame motion of a sub-block of pixels. If the detected motion of the sub-block exceeds a preset or adjustable threshold level, the controller 115 can select the region of interest to surround that sub-block. The components and function of the motion estimation logic 190 are described in detail below in connection with the motion compensation embodiments.

More than one independent region of interest can be selected. For example, regions of interest can be selected, either manually or automatically, around fast moving, slow moving, and intermediate moving portions of the image. Due to the computational complexity involved in using multiple regions of interest, it is presently preferred that the number of selected regions of interest be limited to one or two.

Selectively Applying Imaging Parameters

Figure 3:
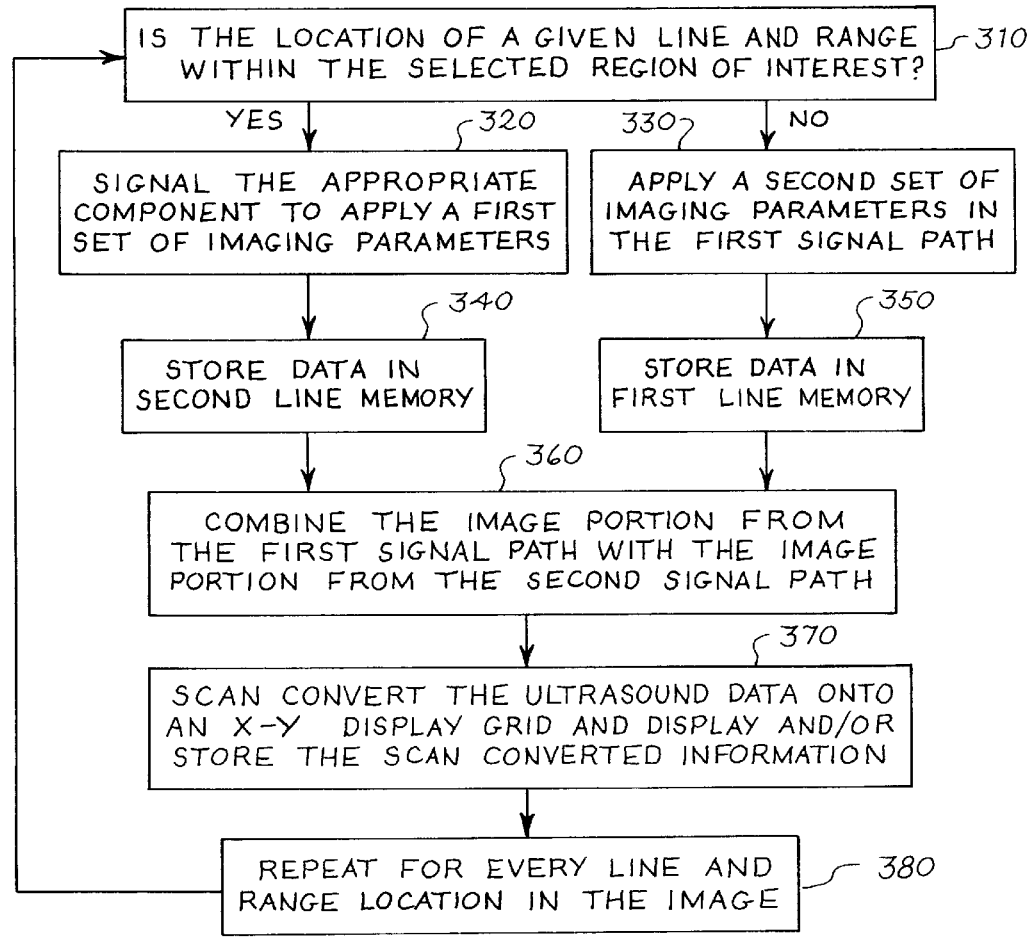
FIG. 3 is a flow chart illustrating how the controller of a system of the preferred embodiment of FIG. 1 controls the system to apply imaging parameters and assemble a composite image.

Once the region of interest is selected, a first set of imaging parameters can be selectively applied inside the region of interest and a different set of imaging parameters can be applied outside the region of interest either manually by the user via the user interface 120 or automatically by the controller 115 (step 220). FIG. 3 is a flow chart showing how the controller 115 controls the operation of the system 110 to apply imaging parameters inside and outside the region of interest. First, a given line and range location is analyzed by the controller 115 to determine whether the location is within the selected region of interest (step 310). If the location is within the selected region of interest, the controller 115 signals the appropriate component (e.g., the beamformers 125, 130, the second processor 155 in the second signal path 145, etc.) to apply a first set of imaging parameters (step 320). For example, for increased line density inside the region, the controller 115 would instruct the transmit beamformer 125 to fire more lines and instruct the receive beamformer 130 to receive more lines within the region of interest.

If the location of the line and range is outside of the selected region of interest, the controller 115 allows the ultrasound data corresponding to that location to pass through the first signal path 140 and a second, different set of imaging parameters is applied (step 330). It is preferred that the image within the region of interest and the image outside the region of interest be in the same imaging mode (e.g., B-mode, color mode, etc.). The signals from the first 150 and second 155 processors are held in the first 160 and second 165 line memories, respectively (steps 340 and 350). The other steps in the flow chart are discussed below. As mentioned below, the above-described steps are repeated for every line and range location in the image (step 380).

As mentioned above, the controller 115 can apply imaging parameters within the region of interest to improve both spatial and temporal resolution within the region of interest. Several imaging parameters can be used, either individually or in combination with one another, to improve spatial resolution. For example, different line densities can be used inside and outside the region of interest. In general, a greater line density provides better spatial resolution (which is desirable when fine structures need to be resolved) but typically results in lower temporal resolution (frame rate). With the system 110 of this preferred embodiment, the controller 115 can instruct the transmit 125 and receive 130 beamformers to send and receive more ultrasound beams within the region of interest than outside the region of interest.

Another imaging parameter that can be applied is the number of transmit foci per scan line. In general, an ultrasound beam has the smallest azimuthal beam width at the transmit focus. Away from the focus, the beam width widens. Since smaller azimuthal widths result in better azimuthal resolution, it is preferred to have small width throughout the range of the region of interest. Increasing the number of transmit foci per ultrasound line will increase the number of locations where the beam widths are small. The impact of having more transmit foci per line is that these lines are transmitted and received from the same direction for as many times as there are number of foci. Increasing the number of transmit foci per line is well known in the art. Generally, the controller 115 instructs the beamformers 125, 130 either to transmit and receive multiple lines from the same spatial location or to advance in the scanning operation.

Ultrasound operating frequency is another imaging parameter that can be applied inside the region of interest. The choice of transmit frequencies involves a tradeoff between spatial resolution and penetration—a higher frequency improves spatial resolution and a lower frequency improves penetration. This tradeoff can be particularly useful when, for example, better spatial resolution is desired inside the region of interest and higher penetration is desired outside the region of interest. The controller 115 controls the frequency being transmitted and the timing of the transmission and additionally synchronizes the other components of the system 110 accordingly.

A different transmit power can also be used within the region of interest. This is especially important when using harmonic-generating agents or conventional contrast agents. If the transmit power is too high, it will destroy the contrast bubbles. If the transmit power is too low, penetration and signal-to-noise ratio will decrease and the second harmonic (non-linear) operation will not activate. By selecting the region of interest around the area that contains the agents, the user can ensure optimal operation. To implement this variation, the controller 115 instructs the transmit beamformer 125 to use different power within the region of interest. The controller 115 preferably adjusts the receive gain in the receive beamformer 130 according to the transmit power to achieve a uniform brightness throughout the scan plane.

Additionally, a logarithmic compression profile in a particular region of interest can be altered. The system 110 has a limited dynamic range, defined as the range between the largest magnitude of signal the system 110 can process and the noise floor set by the system's 110 electronics. Variations in log compression profile determine whether the entire range or a portion of the range is displayed. For example, if a user is only interested in bright targets in a region of interest, a small log compression profile displays only the large magnitude signals in the region of interest. If a user is interested in seeing both bright and weakly reflecting targets in the region of interest, a large log compression profile displays both the large and small magnitude signals.

Another imaging parameter that can be varied is post-processing maps. Post-processing maps transform the scan-converted data to output values that are finally mapped onto the display. Changing post-processing maps alters the range of input signal that are emphasized. Additionally, the number of receive lines per transmit line can vary. Multiple lines of information can be received from slightly different directions following a single transmit operation. Receiving multiple lines of information provides better spatial resolution. In operation, the controller 115 instructs the receive beamformer 130 to receive multiple lines.

Pre- and post-detection filter characteristics can also be varied. Received RF signals can be summed in various ways and can be transformed to IF or baseband signals before summation. The envelope of the summed signal is extracted and stored for scan conversion. Filters can be applied to the summed IF or baseband signals to enhance certain aspects of the image prior to detection. For example, a nonlinear filer based on signal intensity can be applied to smooth-out low-level noise. Different filtering characteristics can be applied prior to or after scan conversion and can be controlled as a function of depth.

Different transmit pulse shapes can also be used. A transmit pulse shape refers to the number of cycles in the transmit burst. It also refers to a different Gaussian pulse bandwidth. In general, a transmit pulse shape can be chosen for the region of interest to reduce signal attenuation as the signal propagates through tissue.

Additionally, a different receive frequency band can be used within the region. For example, harmonic frequencies (frequencies associated with non-linear propagation or scattering of transmit signals) can be received within the region of interest. As-used herein, harmonic includes subharmonics as well as second, third, fourth, and other harmonics. Second harmonic frequencies produce ultrasound images with dramatically reduced acoustic clutter and better beamforming than the fundamental image counterpart.

In addition to or in combination with applying imaging parameters to improve spatial resolution, imaging parameters can be applied to improve temporal resolution within the region of interest. One way in which temporal resolution can be improved is by increasing the frame rate inside the region of interest by acquiring additional real (i.e., non-interpolated) ultrasound-image frames within the region of interest. It is preferred that real frames be acquired for regions that contain contrast agents, especially those that radiate energy at the second harmonic.

Temporal resolution can also be improved by using a different persistence level inside the region of interest than outside the region of interest. Persistence inside the region of interest can be a function of image motion. As used herein, the term "image motion" refers to motion within an ultrasound image such as, but not limited to, tissue motion and motion of contrast agents. As described in more detail below, motion can be detected by using motion estimates of a sub-block of moving pixels or by computing the difference between pixels at the same spatial location in successive frames. If there is significant image motion, it is preferred that persistence be reduced to avoid smearing or blurring of the moving object. Similarly, if there is very little image motion, it is preferred that persistence be increased to average out noise in the image, thereby increasing signal-to-noise ratio. As discussed below, persistence inside the region of interest can be varied using the techniques of motion-compensated persistence with motion-compensated interpolated frames, motion-compensated persistence with real ultrasound frames, and motion-adaptive persistence.

One way in which persistence inside the region of interest can be varied is by using motion-compensated persistence with motion-compensated interpolated frames. (The generation of motion-compensated interpolated image regions is described in the Motion Compensation Embodiments section below.) In this technique, interpolated frames are generated to spatially coordinate the position of moving objects in the image. For example, suppose an output image frame comprises a summation of three image frames—frame N, frame N−1, frame N−2. Also suppose that the motion estimation logic 190 detects object motion of 4 pixels to the right in each of the image frames. Motion-compensated interpolated image frames can be generated, as described below, so that the three frames being weighted are frame N, frame N−1 with the moving object translated 4 pixels to the right, and frame N−2 with the moving object translated 8 pixels to the right. In this way, the moving object in each of the three frames would be located in the same spatial position before summing the three frames to generate an output frame, thereby avoiding the problem of object blurring.

While only one moving object was used in the example above, it is important to note that different motion vectors can be computed for different parts of the image so several moving objects can be similarly analyzed. In this way, in addition to avoiding the problem of object blurring, noise will be reduced in the same amount in both moving and non-moving areas of the image.

Another way in which persistence inside the region of interest can be varied is by using motion-compensated persistence with real ultrasound frames. This technique is similar to the first technique described above in that motion vectors can be computed for different parts of the image, but instead of generating a motion-compensated interpolated frame, the persistence filter determines which pixels to process. That is, in the first technique, motion estimates are used to create motion-compensated interpolated frames to align moving objects in an image. The persistence filter in the first technique processes pixels corresponding to the same spatial location across a number of frames. In this technique, the spatial locations employed by the persistence filter are determined by the motion estimates. That is, motion estimates are used to determine the location of a moving block of pixels, and that location is used by the persistence filter. In this way, pixels that belong to the same object are filtered. When there is no motion is present, the filter uses the same spatial location, as in the case of a conventional persistence filter. As with the first technique, this technique provides the advantages of reducing blur and of reducing noise in the same amount in both moving and non-moving areas of the image. Because motion estimates employed in this technique, the same motion estimates can be used to generate motion-compensated interpolated frames, thereby reducing computation time by avoiding recomputation of motion estimates.

It is important to note that in both the first and second technique, a non-recursive procedure (i.e., each output being a weighed sum of input frames) or a recursive procedure (i.e., each output frame being a weighed combination of input and previous output frames) can be used. It is also important to note that in both the first and second technique, the persistence filter coefficient in all or part of the image frame can vary as a function of image motion.

The third technique that can be used to vary persistence as a function of image motion is motion-adaptive persistence. Motion-adaptive persistence can be used with the techniques described above to vary the persistence filter coefficient in all or part of the image frame as a function of image motion. Motion-adaptive persistence can also be used with other persistence techniques. Motion-adaptive persistence will be described in reference to FIG. 4A, which shows an operational block diagram of a persistence filter using a recursive procedure. As shown in this figure, an output frame O(n) is generated by adding the intensity of each pixel in a region in the previous output frame O(n−1), multiplied by a persistence filter coefficient $\alpha(n)$, with the intensity of each corresponding pixel in a region of the input frame I(n), multiplied by $(1-\alpha(n))$. The persistence filter coefficient $\alpha(n)$ can be recalculated on a frame-by-frame basis or repeated after a number of frames (e.g., once every 10 frames).

A persistence-filter-coefficient generator 450 generates a persistence filter coefficient $\alpha(n)$ for the region of interest from the previous ultrasound-image frame O(n−1) and the current ultrasound-image input frame I(n). Next, a first multiplier 470 multiplies the persistence filter coefficient $\alpha(n)$ with previous ultrasound image frame $\alpha(n-1)$ to form a modified previous ultrasound image frame O'(n−1) in a region of interest. A second multiplier 475 multiples the input ultrasound image frame I(n) with $(1-\alpha(n))$ to create a modified input frame I'(n). Finally, adder 490 adds the pixel intensity of each pixel in the region of interest in the modified input frame I'(n) with the pixel intensity of each pixel in the region of interest in the previous ultrasound-image frame O(n−1) to generate an enhanced region of interest in the current ultrasound-image output frame O(n). The operations shown in this diagram can be implemented in the controller 115, for example.

In using motion-adaptive persistence, the persistence filter coefficient $\alpha(n)$ varies as a function of image motion. Specifically, the persistence filter coefficient $\alpha(n)$ increases as the level of motion within the region decreases. FIG. 4B illustrates such a relation for three different filter designs 492, 494, 496, although others designs can be used. As shown in FIG. 4B, the persistence filter coefficient $\alpha(n)$ increases as d decreases. The function d can be computed by using motion estimates of a sub-block of moving pixels or by computing the difference between pixels at the same spatial location in successive frames. The function d preferably is derived from motion estimates of sub-blocks of pixels determined to give the best match between a region in the previous frame O(n−1) and the current image frame I(n). This motion vector is the value (x,y) which gives the minimum sum of absolute differences and may be derived at high speed using a L64720A motion estimator or a similarly programmed TMS320C80 processor. Technically, the net motion length is the square root of $(x^2+y^2)$, where x and y are the pixel shifts required to obtain the best match.

An advantage of this implementation is that the sum of absolute differences is an error signal related to noise in the image. If the detected motion is small or varies randomly between sequences and the sum of absolute differences is larger than a threshold, the image is probably stationary and noisy. Persistence could then, accordingly, be increased.

As mentioned above, the function d can also be computed by computing the difference between pixels at the same spatial location in successive frames—an indication of image movement. That is, if motion is present, it is likely that the pixel values will change from frame to frame. Specifically, the function d can be given by the following equation:

$$d(I(n), O(n-1)) = \sum_{(x,y) \text{ in } A(i,j)} \frac{(I(n, x, y) - O(n-1, x, y))^2}{(I(n, x, y) - O(n-1, x, y))^2}.$$

wherein I(n,x,y) comprises an intensity value of a pixel in the current ultrasound-image input frame, O(n−1,x,y) comprises an intensity value of a pixel in a previous ultrasound-image output frame, and "(x,y) in A(i,j)" comprises every pixel (x,y) in an area A(i,j) in the selected region of interest. It is important to note that other equations can be used to represent the function d.

There are several alternatives. First, instead of comprising every pixel in the region of interest, area A(i,j) can comprise a subset of the pixels in the region of interest to reduce the amount of computation. In this alternative, area A(i,j) can be located around the center of the region or can comprise pixels that have an intensity amplitude greater than a predetermined threshold. Even though some of the pixels were not used in computing the coefficient α(n), the generated persistence filter coefficient α(n) can still be applied to all pixels in the region.

As another alternative, more than one region can be selected. For instance, the user can select more than one region of interest. Preferably, if multiple regions are required, selection is based on automatic measurement, for example, of regions with low or high motion. Alternatively, the entire image frame can be divided into regions, and the calculation and applications discussed above can be applied over the entire image frame through each of the regions. If the persistence filter coefficient α(n) is computed for multiple regions, the particular persistence filter coefficient applied to a specific pixel in the frame can be computed by linearly interpolating among the persistence filter coefficients of adjacent regions based on, for example, the pixel's distance from a particular point (e.g., the center) of each region.

There can be situations in which the value of d is high even though most pixels in the region are below a certain intensity value. Such a situation arises due to noise in the region, not object motion. If the minimum-sum-of-absolute-differences method is used, situations in which d is small or randomly varying and the sum-of-absolute differences is large indicate noise and little motion. In these situations, the persistence filter coefficient α(n) can be assigned a high value to average out the noise, thus improving the signal-to-noise ratio for the region.

There are several advantages to varying persistence as a function of image motion. First, by reducing persistence when the image exhibits motion, spatial resolution is preserved. Similarly, by increasing persistence when the image exhibits little or no motion, the signal-to-noise ratio for the region is increased by averaging out noise. By using a plurality of regions across the image frame, the signal-to-noise ratio can be improved over stationary and high noise regions, while preserving the spatial resolution in regions of the frame exhibiting motion. Additionally, the tissue motion imaging modes such as DTV and DTE are improved by preventing blackouts when a tissue is stationary.

Assembling the Composite Image

After the different sets of imaging parameters are applied inside and outside the region of interest, the image combination logic 170 combines a first image portion within the region of interest with a second image portion outside the region of interest to form a composite image, as shown in step 230 in FIG. 2 and in step 360 in the flow chart of FIG. 3. If a particular line and range location is within the selected region of interest, the image combination logic 170 selects data from the second signal path 145. Alternatively, if a particular line and range location is outside the selected region of interest, the image combination logic 170 selects data from the first signal path 140. In this way, the image combination logic 170 controls what image data will be sent to the scan converter 175.

Lastly, the scan converter 175 converts the ultrasound data onto an x-y display grid and displays the converted information on the display 185 and/or stores the converted information in the image memory 180 (step 370). This process is repeated for every line and range location in the image (step 380). At the completion of this process, the display 185 presents a composite image comprising a first image portion within the region of interest and a second image portion outside the region of interest. The image combination logic 170 and the controller 115 can additionally comprise hardware or software to present a temporally and spatially smooth composite image, as described below.

Temporal Smoothing

When the actual frame rate inside the region of interest is greater than the actual frame rate outside the region of interest, the apparent frame rate of the image outside the region of interest can be increased to give the composite image the appearance of having a single frame rate. To match the frame rates, the ultrasound system 110 inserts interpolated frames between real frames outside the region of interest.

First, the motion estimation logic 190 measures motion between at least two real ultrasound-image frames outside of the region of interest by detecting frame-to-frame motion of a sub-block of pixels. Next, the motion estimation logic 190 generates motion-compensated interpolated frames outside the region of interest, which are then inserted between the real ultrasound image frames. This method is more completely described below in the Motion Compensation Embodiments section.

By using this method to give the composite image the appearance of having a single frame rate, considerable time savings are obtained when compared to the time needed to acquire a real image for the entire frame. For example, if a selected region of interest comprises 10% of the total image dimension and the time required for acquiring a real frame is 100 ms, 10 ms are needed to capture an additional real image within the region of interest. Hence, the time needed to capture two real frames for the entire image dimension (100 ms+100 ms=200 ms, or 100 ms per final displayed frame) is considerably greater than the time needed to capture one real frame for the entire image dimension and an additional real frame within the region of interest (100 ms+10 ms=110 ms, or 55 ms per final displayed frame), assuming that the time required for frame interpolation is negligible.

This method of temporally smoothing the composite image can also be applied with more than one independent region of interest. For example, if three regions are selected and the frame intervals of the regions are enhanced to 200 ms, 100 ms, and 50 ms, respectively, then the composite image should have an apparent overall frame rate matching the highest actual frame rate (50 ms for this example). The apparent frame rate of the non-enhanced image outside of the regions is increased as described above. Additionally, interpolated frames can be inserted into the two other regions of interest to increase their apparent frame rate to 50 ms.

In performing the temporal smoothing method described above, if an accurate measurement of motion cannot be made, the ultrasound system can acquire additional real ultrasound-image frames instead of generating an interpolated frame. The accuracy of the measurement can be assessed by comparing a pixel error signal of the measured motion against a threshold level, as will be described in greater detail below.

Instead of using motion-compensated interpolated frames to affect temporal smoothing, the image data outside the region of interest can be repeated to match the frame rate of the image inside the region of interest. Unlike the method of temporal smoothing using motion-compensated interpolated frames, this method does not present new image information to the user. Technically, it is necessary to delay the display of frames so that the interpolated frames can be calculated from the frame before and the frame after. However, the delay of a couple of frames will not generally be noticeable to the user.

Spatial Smoothing

To form a spatially smooth composite image, a smooth transition can be created between the first and second image portions. A smooth transition can be formed by summing a fraction of the first image portion with a fraction of the second image portion at the boundaries of the region of interest. Referring now to FIG. 5, preferably, in the region 530, the pixel locations closest to region 510 are determined by a weighted sum of image data from the first and the second image data, wherein the first image data is emphasized, while at a location closest to region 520, the second image data is emphasized (i.e., linear interpolation of the first and second data depending on position). Another way to spatially smooth the composite image is to apply a low-pass filter (for example, within four pixels from the boundary) to reduce artifacts. Additional artifact reduction methods are described below.

Figure 6:
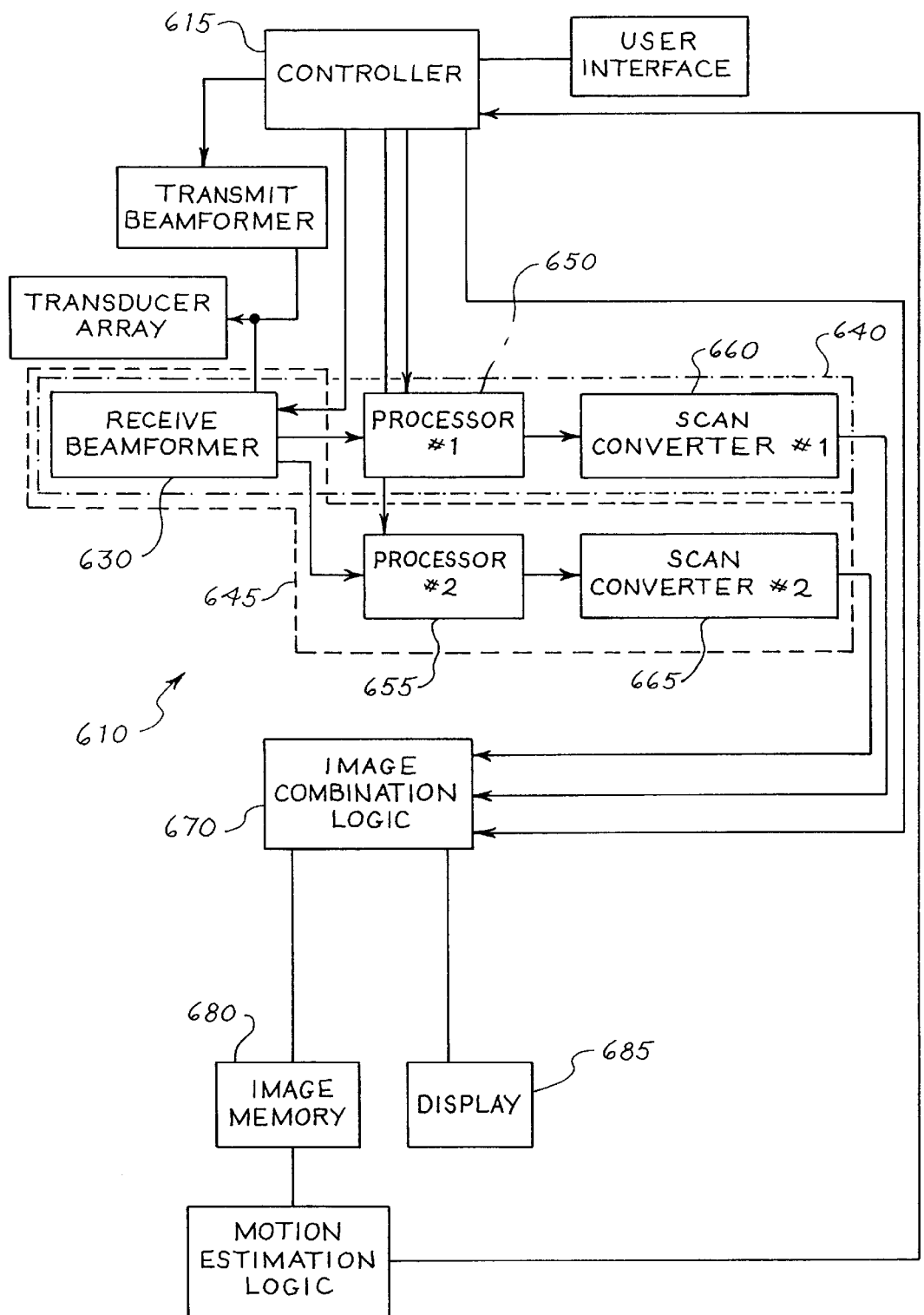
FIG. 6 is a block diagram of a first alternative ultrasound imaging system.
Figure 7:
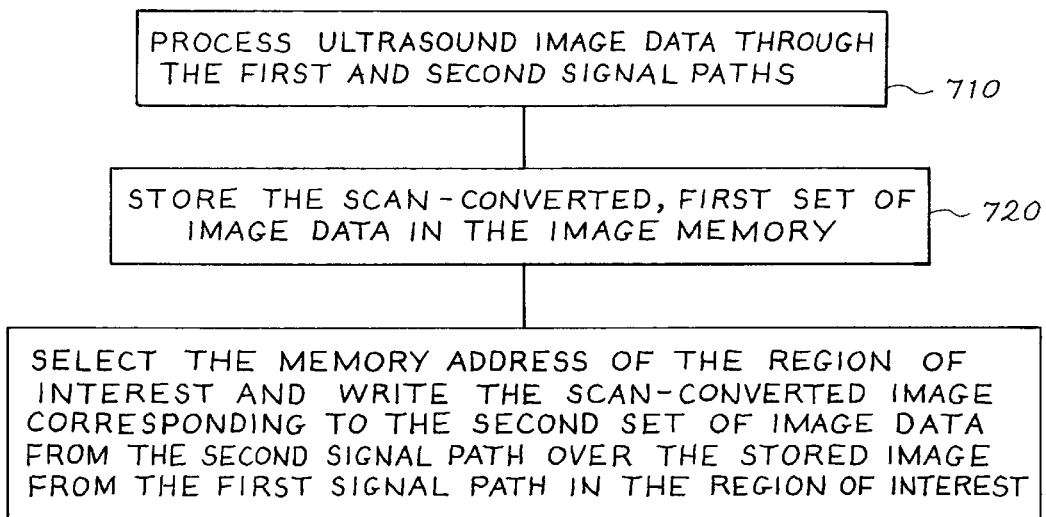
FIG. 7 is a flow chart illustrating how a controller of the first alternative system controls the system to vary imaging parameters.

There are several alternatives to the above-described system 110. FIG. 6 shows one alternative system 610. The two systems 110, 610 have several common components, which will not be further described here. However, in addition to the receive beamformer 630, the signal paths 640, 645 of this system 610 contain a first and second processor 650, 655 and a first and second scan converter 660, 665 respectively. FIG. 7 is a flow chart showing how the controller 615 controls operation of the system 610 to selectively apply sets of imaging parameters.

First, ultrasound image data is processed through the first 640 and second 645 signal paths (step 710). In the first signal path 640, a first set of image data for the entire scan region is processed by the first processor 650 and scan converted onto an x-y display grid by the first scan converter 660. In the second signal path 645, a second set of image data within the region of interest is processed by the second processor 655 and scan converted onto an x-y display grid by the second scan converter 665. As with the above-described system 110, the controller 615 analyzes a given line and range location to determine whether it is within the selected region of interest and, accordingly, what set of imaging parameters to apply. Next, the image combination logic 670 stores the scan-converted, first set of image data in the image memory 680 (step 720). The image combination logic 670 then selects the memory address of the region of interest and writes the scan-converted image corresponding to the second set of image data from the second signal path 645 over the stored image from the first signal path 640 in that region (step 730) to form a composite image. This composite image can then be presented to the user via the display 685 and/or stored.

Figure 8:
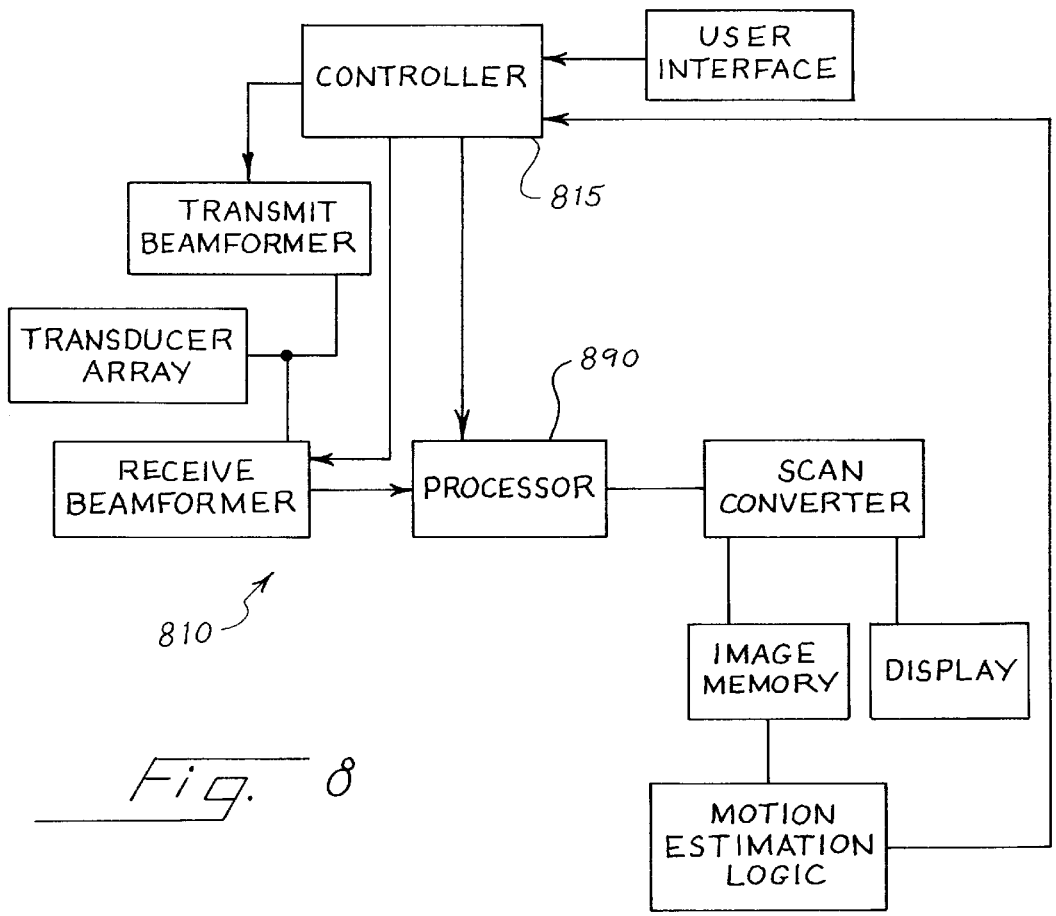
FIG. 8 is a block diagram of a second alternative ultrasound imaging system.

FIG. 8 shows a second alternative system 810 to the above-described ultrasound imaging system 110. The two systems 110, 810 also have several common components, which will not be further described here. In this system 810, however, only one signal path, which contains a processor 890, is used. As with the above systems 110, 610, the controller 815 analyzes a given line and range location to determine whether it is within the selected region of interest. Based on that determination, the controller 815 signals the processor 890 to apply certain imaging parameters.

It is important to note that in all of the above-described systems, as well as the systems of the preferred embodiments below, additional components may be added to the system and described functions can be implemented with one or more components of the system.

MOTION COMPENSATION EMBODIMENTS

Figure 9:
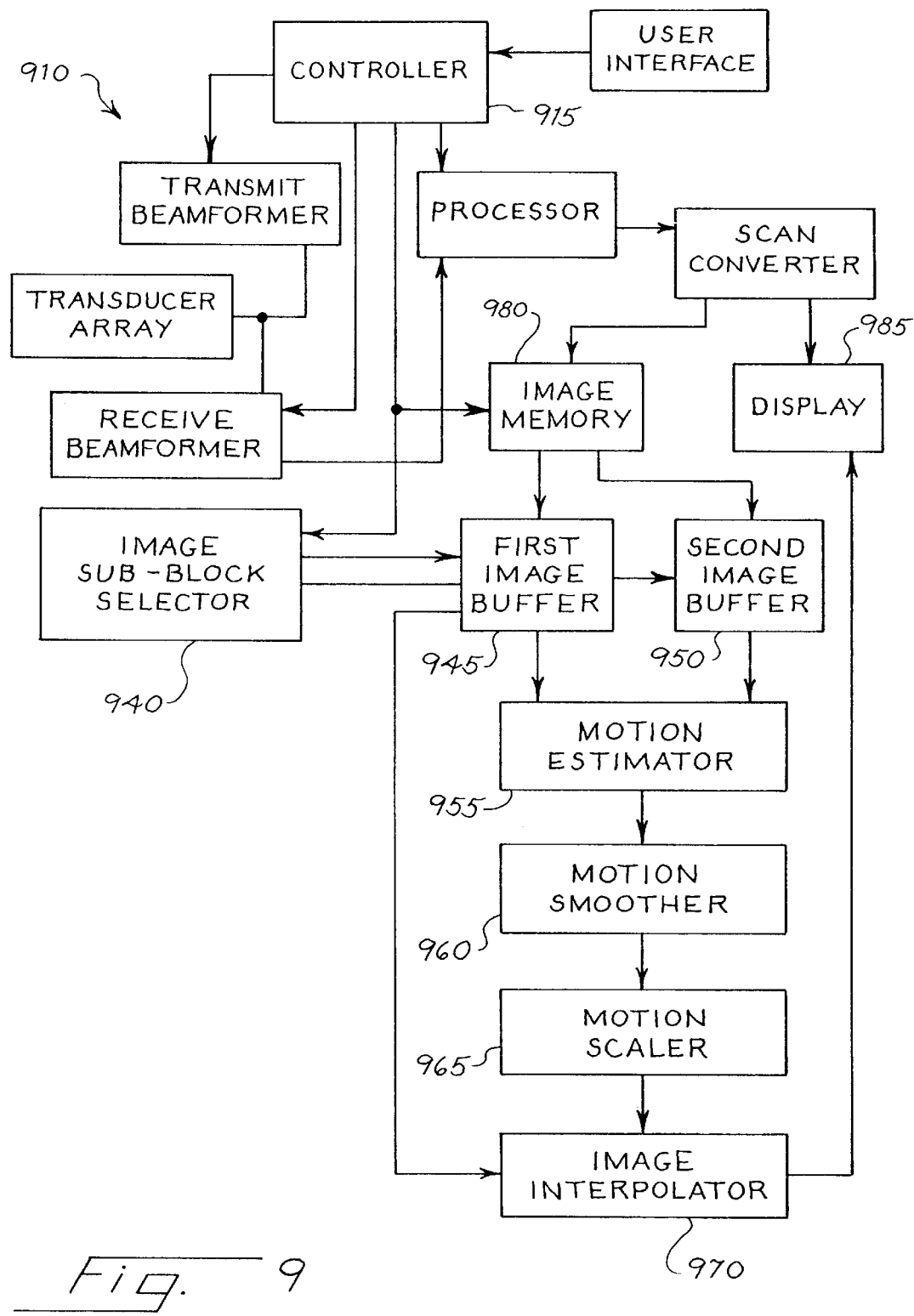
FIG. 9 is a block diagram of an ultrasound imaging system of another preferred embodiment.

FIG. 9 is a block diagram of an ultrasound imaging system 910 that comprises means for generating a motion-compensated interpolated image inside a region of interest in response to measured image motion. As mentioned above, the term "image motion" refers to motion within an ultrasound image such as, but not limited to, tissue motion and motion of contrast agents. This system 910 is configured similarly to that of the alternate system 810 of the composite image embodiments. FIG. 9 additionally shows the components of the motion estimation logic described in the composite image embodiments. Specifically, an image sub-block selector 940 is provided, which is responsive to the controller 915 and is coupled to a first 945 and second 950 image buffer. The first 945 and second 950 image buffers are responsive to the image memory 980 and are coupled to a motion estimator 955. The motion estimator 955 is coupled to a motion smoother 960, which is coupled to a motion scaler 965. An image interpolator 970 is responsive to the motion scaler 965 and the first image buffer 945 and is coupled to the display 985. The specific function of these components will be described below.

Figure 10:
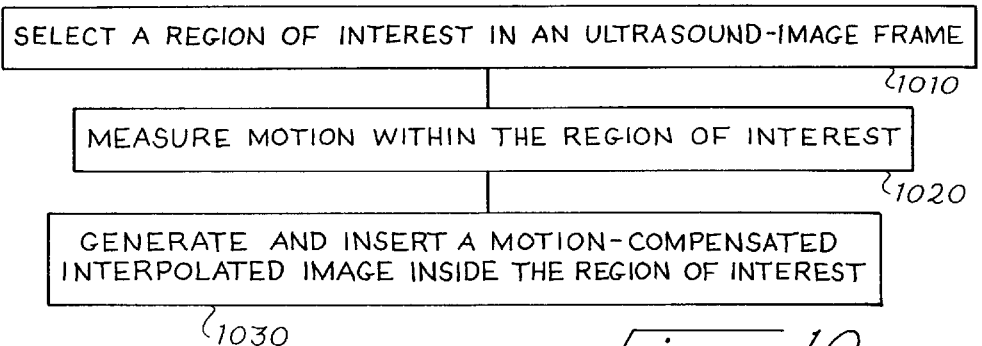
FIG. 10 is a flow chart illustrating a method for increasing an apparent frame rate within a region of interest in an ultrasound image by generating motion-compensated interpolated images.

The system 910 of this preferred embodiment can implement a method for increasing the apparent frame rate within a region of interest in an ultrasound image by generating motion-compensated interpolated images, as illustrated in FIG. 10. First, a region of interest in an ultrasound-image frame is selected (step 1010). Next, motion within the region of interest is measured (step 1020). Based on this measured motion, a motion-compensated interpolated image is generated and inserted between real ultrasound-image frames inside the region of interest (step 1030). By using this method, the ultrasound system 910 increases the apparent frame rate within the region of interest. The steps of this method, which will be described in more detail below, can be performed in real time.

First, a region of interest in an ultrasound-image frame is selected (step 1010). The region of interest can comprise all or a portion of the ultrasound image and can either be manually selected by the user or automatically selected, as discussed above in the Composite Image Embodiments section. Also as discussed in the Composite Image Embodiments section, multiple regions of interest can be selected.

Next, motion within the region of interest in measured (step 1020). Motion can be measured, between two image frames (i.e., image frame N and image frame N+1). These two frames, which are initially held in the image memory 980, are stored in the first and second image buffers 945, 950, respectively. Images are preferably stored in the image memory 980 and the frame buffers 945, 950 as 8-bit gray scale values at full pixel density.

To measure motion, the motion estimator 955 performs an image tracking operation to find estimated pixel motion of a selected sub-block of pixels from image frame N to image frame N+1. To measure motion, the motion estimator 955, which preferably includes a L64720A motion estimator from LSI Logic, performs a minimum-sum-of-absolute differences operation, as is well known in the art. Alternatively, a high power, programmed digital signal processing circuit, such as a TMS320C80 circuit by Texas Instruments, can be used.

The image sub-block selector 940 determines which sub-blocks of the image frame will be sent to the motion estimator 955. A sub-block may be, for example, an 8×8, 16×16, 32×32, or 48×48 block of pixels from a 512×512 pixel frame. It is presently preferred that a 32×32 or a 16×16 block of pixels be used. Larger pixel blocks (such as a 32×32 block) may require multiple motion estimators to be cascaded. The controller 915 repeats the motion estimation process for all the sub-blocks in image frame N, thereby generating motion estimates over the entire ultrasound image. Because motion estimates for adjacent sub-blocks are typically similar, the motion smoother 960 can create the appearance of smooth sub-block motion by averaging the motion estimates.

Lastly, based on the measured motion, a motion-compensated interpolated image is generated and inserted between real ultrasound-image frames inside the region of interest (step 1030). In this step, the motion scaler 965 scales the motion estimate according to the number of interpolated frames that need to be generated. For example, if a user desires to double the apparent frame rate, one interpolated frame will be generated for insertion between image N and image N+1, and the scaling factor will be 0.5. If three frames are being inserted, the scaling factors of 0.25, 0.5, and 0.75 are used for successive motion interpolation steps. The image interpolator 970 takes the selected sub-block data from image frame N in the first image buffer 945 and applies the scaled motion. That is, the image interpolator 970 changes the pixel address for every pixel in the sub-block by the required amount and accumulates the result. This process is then repeated for all sub-blocks in the image frame. The interpolated frame can then be inserted between the two real frames, as is known in the art, and presented to the user on the display 985.

As an example, consider the situation in which one interpolated frame is to be generated and the motion estimator 955 determines that a 32×32 sub-block of pixels (initially located at locations (0-31, 0-31) in image frame N) moved 8 pixels to the right and 8 pixels down. Because only one frame will be inserted, the factor used by the motion scaler 965 is 0.5. Accordingly, the scaled motion estimate is 4 pixels (0.5*8) to the right and 4 pixels (0.5*8) down. Thus, the pixel sub-block will be placed at locations (4-35, 4-35) in the interpolated frame. As discussed further below, it is also possible to add a component due to the N+1 frame. In this case, the required motion is 4 pixels to the left and 4 pixels up, so that, theoretically, the interpolated frame N and frame N+1 are superimposed.

By moving sub-blocks in this manner, it is possible that repositioned sub-blocks will overlap in the interpolated image frame. To deal with the overlap problem, the pixel data in the region of overlap can be averaged or the data from one of the sub-blocks can be given priority.

Another problem which can arise when sub-blocks are moved is that there can be pixel locations in the interpolated image frame that do not contain new pixel data (i.e., "holes" are formed in the interpolated image frame). One approach to dealing with holes is to eliminate the possibility of their creation. That is, sub-blocks can be written over a copy of a real image frame (e.g., image frame N or image frame N+1). In this way, there will always be pixel information at every pixel location of the interpolated image frame even if some locations in the interpolated image frame do not contain new data. Another approach is to fill the holes with pixel information interpolated from surrounding sub-blocks.

There are several advantages to using this method. First, this method increases the apparent frame rate of an ultrasound imaging system beyond the limitations normally imposed by, for example, line density, transit time, and Doppler processing delays. Because there is considerable redundancy between consecutive frames, image quality in many cases will not suffer as a result of inserting interpolated frames.

Second, unlike applying a conventional interpolation filter, this method takes account of frame-to-frame motion and does not result in blurred images when the target moves. As a result, motion-compensated interpolated images can be used in applications in which a high frame rate is important.

Another advantage is that this method permits the use of lower channel cable counts in situations where high channel counts would otherwise be required. For example, phase-aberration corrected images may require very high physical transducer element counts in 1.5 or 2 dimensional arrays. Since cable costs (and termination costs in particular) can be prohibitively expensive, a potential option is to multiplex, for example, half the array in one firing and the other half in the next firing. This multiplexing can be performed on a line-by-line basis rather than a frame-by-frame basis and is preferably performed by using multiples of the HV2xx family of multiplexers from Supertex, Inc. (Sunnyvale, Calif.) or other suitable circuitry. With this multiplexing, not only is the cable channel count halved, but the frame rate is also halved. By using the method of this preferred embodiment, full apparent frame rate can be achieved even with using lower channel cable counts. Additionally, this method can be used in a three-dimensional volume scan from a two-dimensional array where frame rate will be very slow.

Lastly, this method is easily implemented since image frame motion analysis is largely a subset of the video operations (e.g., Moving-Picture-Experts-Group (MPEG) operations) which are already available in chip set solutions from multiple vendors, such as LSI Logic or C-Cube, for real-time motion-detection operations. Such motion analysis is described in more detail below.

While the above method has been described in terms of scan-converted images, the motion estimations can be applied to raw acoustic line data (envelope detected, RF, or baseband In phase/Quadrature data), using the known geometry of the lines (e.g., polar) to convert to required pixel translations (i.e., Cartesian). However, the method described above is preferred on the grounds of simplicity.

As an alternative to the above, a real frame (instead of an interpolated frame) can be acquired when an inaccurate, interpolated frame is generated. As described below, motion estimators that are compatible with MPEG compression standards typically supply pixel error signals. If the correlation of one frame block to the next is poor, the sum of the error signals will be large, indicating that the interpolated frame is inaccurate. To prevent the display of an inaccurate frame, if the sum of the error signals exceeds some preset or adjustable threshold level, the ultrasound system 910 can acquire additional real images inside the region of interest instead of generating an interpolated frame.

As another alternative, when the region of interest comprises less than the entire image and when motion-compensated interpolated frames are used inside the region of interest, image data outside the region of interest can be repeated to match the frame rate of the image inside the region of interest.

ADAPTIVE MOTION-SENSING EMBODIMENTS

Figure 11:
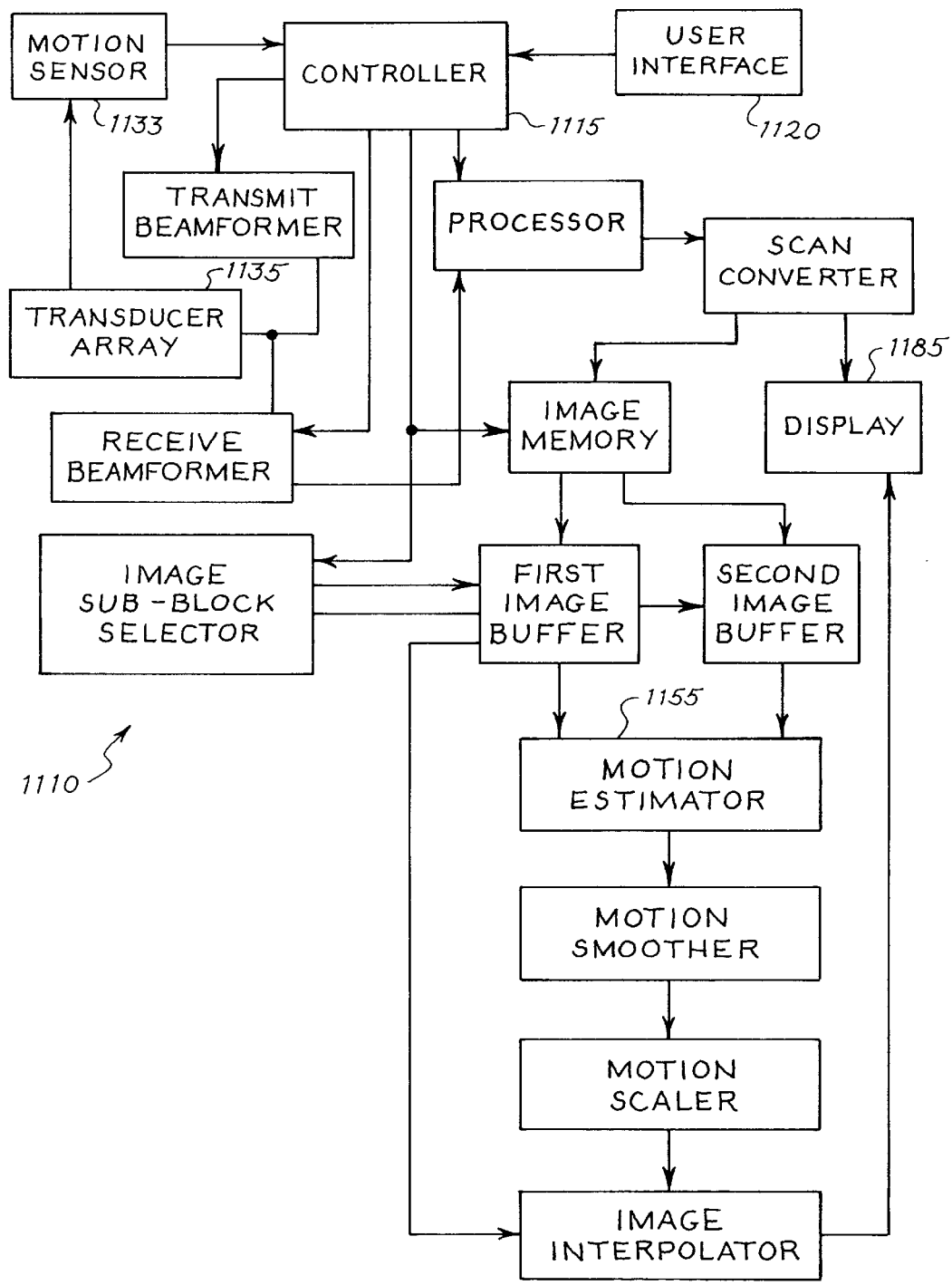
FIG. 11 is a block diagram of an ultrasound imaging system of another embodiment.

The system 1110 illustrated in FIG. 11 has a configuration similar to that of the motion compensation embodiments and additionally comprises a motion sensor 1133. The motion sensor 1133, which is responsive to movement of a housing of the transducer array 1135 and is coupled to the controller 1115, measures motion of the transducer probe. The controller 1115 of this preferred embodiment comprises means for altering system parameters in response to the presence or absence of detected motion. Specifically, the controller 1115 comprises means for automatically applying certain imaging parameters within a region of interest of an ultrasound-image frame in response to detected image or transducer motion and means for automatically altering the operating mode of the transducer array 1135 in response to an absence of detected transducer motion. These two controller 1115 functions, which can be performed in real time, will be described in more detail below.

Automatically Applying Imaging Parameters

Figure 12:
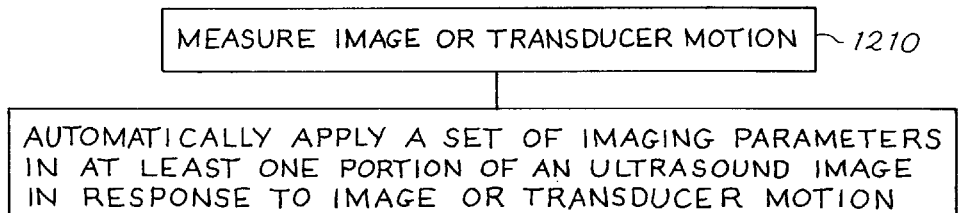
FIG. 12 is a flow chart illustrating a method for automatically adjusting imaging parameters in a region of interest in an ultrasound image in response to detected transducer or image motion.

As mentioned above, many users fail to optimize imaging parameters after image or transducer motion because of the complexity of the required adjustment. This imaging system 1110 solves that problem by automatically applying certain imaging parameters in a region of interest in an ultrasound image in response to detected transducer or image motion. As illustrated in FIG. 12, first, image or transducer motion is measured (step 1210). Then, the controller 1115 automatically applies certain imaging parameters in at least one portion of an ultrasound image in response to the measured motion (step 1220).

The first step in the method of this preferred embodiment is to measure transducer or image motion (step 1210). Preferably, the motion estimator 1155 measures motion of a sub-block of pixels between two ultrasound-image frames, as described in the Motion Compensation Embodiments section and below. This measured motion is indicative of transducer motion and image motion. Motion estimates can be taken in one or more portions of the image frame. If motion estimates are taken in more than one portion of the image, the controller 1115 preferably bases the decision of whether to varying the imaging parameters on whether the measured motion of a majority of the portions exceeds a threshold. More weight can be attached to the motion estimates derived in the middle of the image rather than at the sides since the user is usually most interested in that section of the image frame.

Transducer motion can also be measured by a motion sensor 1133 in the housing of the transducer array 1135. The motion sensor 1133 can be an accelerometer or a magnetic position sensor, such as a "Flock of Birds" magnetic position sensor from Ascension Technology Corporation (Burlington, Vt.).

In response to the measured motion, the controller 1115 automatically applies certain imaging parameters in a region of interest in the ultrasound-image frame to optimize system performance (step 1220). As described in the first two preferred embodiments above, a region of interest can comprise all or part of the frame and can be manually or automatically selected. It is preferred that a single region of interest automatically selected to cover all of the image frame be used to ensure that imaging parameters are applied over the entire image frame in response to measured motion. Additionally, more than one region of interest can be selected.

In operation, if the measured motion exceeds a predetermined threshold, the controller 1115 automatically switches to a higher frame rate/lower spatial resolution mode. In such a mode, imaging parameters are automatically applied in the region of interest to improve temporal resolution to avoid image blurring. If the measured motion is below a predetermined threshold, the controller 1115 automatically switches to a lower frame rate/higher spatial resolution mode. In this mode, imaging parameters are automatically applied in the region of interest to improve spatial resolution. The Composite Image Embodiments section discusses a number of imaging parameters that can be applied to improve spatial or temporal resolution. Specifically, these parameters include: line density, number of transmit foci per scan line, pre-detection filter characteristics, post-detection filter characteristics, post-processing maps, ultrasound operating frequency, transmit power, logarithmic compression profiles, numbers of multiple receive lines per transmit line, transmit pulse shape, receive frequency band, and persistence.

For example, if the image exhibits signs of fast motion (e.g., the user is performing a sweeping search across the body or a tissue is quickly moving), the controller 1115 automatically applies parameters corresponding to a higher speed/lower resolution mode in order to take account of the movement, thereby avoiding the presentation of a blurred moving image. Conversely, if the image exhibits signs of very little motion (e.g., the user is concentrating on a region of great interest or a tissue that is relatively still), the controller 1115 automatically applies parameters corresponding to a lower frame rate/higher spatial resolution mode to provide a more spatially-detailed display.

If the controller 1115 is frequently toggling between higher and lower spatial resolution modes, the displayed image can be difficult to view. Accordingly, it is preferred that the controller 1115 take motion estimates over a sequence of image frames and compare the average of these estimates to a threshold value. In this way, the controller 1115 automatically switches imaging parameters after detecting a sequence of frames of high motion, for example, instead of after detecting the first frame of high motion. It is also preferred that the controller 1115 have an option to disable operation of this method, especially when a transducer probe is mostly stationary but occasional rapid motions are anticipated.

As discussed above, when there is little detected motion, the controller 1115 automatically decreases frame acquisition and increases spatial resolution. To increase the apparent frame rate when the actual frame rate is decreased, the methods of the Motion Compensation Embodiments section can be used to insert motion-compensated interpolated frames between real frames.

Automatically Altering the Operating Mode of the Transducer Array

The controller 1115 of this system 1110 can additionally comprise means for automatically altering the operation mode of the transducer array 1135 in response to an absence of detected image motion. As mentioned above, the motion estimator 1160 can identify motion in the image, typically by measuring motion of a sub-block of pixels between two ultrasound-image frames using, for example, a minimum-sum-of-absolute-differences operation. Zero motion between successive frames indicates that the probe containing the transducer array 1135 is not in use.

If the controller 1115 does not receive signals indicative of transducer motion for a given amount of time (e.g., one minute), the controller 1115 alters the operating mode of the transducer array 1135. For example, the controller 1115 can completely remove power from the transducer array 1135 or can place the transducer array 1135 in a "sleep" mode—an imaging mode using less power. For example, during "sleep" mode, the controller 115 can disable only the imaging modes that cause elevated temperatures in the transducer array 1135. Alternatively, during the "sleep" mode, the system 1115 can acquire real image data at a very low rate (e.g., once per second) until motion is detected. Once motion is detected, fill power can be restored to the transducer array 1135, and the pre-"sleep" operating mode of the transducer array 1135 can be resumed. Additionally, a user can exit the "sleep" mode manually by entering an input to the user interface 1120 (e.g., striking a key on a keyboard).

The controller 1115 can alert a user that the operating mode of the transducer array 1135 has been altered by, for example, displaying a message on the display 1185. The controller 1115 can also synchronize the system 1110 to ensure that the motion estimator 1155 is analyzing the appropriate image frames (i.e., ensuring that image repeated displayed in a "freeze frame" operation are not analyzed for motion).

Since the system 1110 is responsive to any motion, it is not necessary to search for two-dimensional motion. Single acoustic line data can be used to perform one-dimensional correlations between successively acquired lines to determine if the position of peak cross-correlation is non-zero and/or if the peak correlation value is high (as would be the case when there is no image motion). The position of the cross-correlation repeatedly being zero indicates that no probe motion has occurred. This method of detecting motion is much less computationally intensive than methods that compare pixels on a point-to-point basis over the image.

By using the method and system of this preferred embodiment, the problem of transducer overheating is avoided. Unlike past solutions to the problem, using ultrasound-image frame information to measure transducer motion is inexpensive and does not require modifications to be made to the probe housing the transducer array or user intervention. Additionally, because motion estimates are used, this method can be much less computationally intensive than methods that compare pixels on a point-to-point basis over the image. Also, if a system is calculating motion estimates for other functions (for example, for generating motion-compensated interpolated frames), those motion estimates can be used to detect transducer motion, further making this technique less computationally intensive than techniques that use point-to-point comparisons.

DISTORTION CORRECTING EMBODIMENTS

Figure 13:
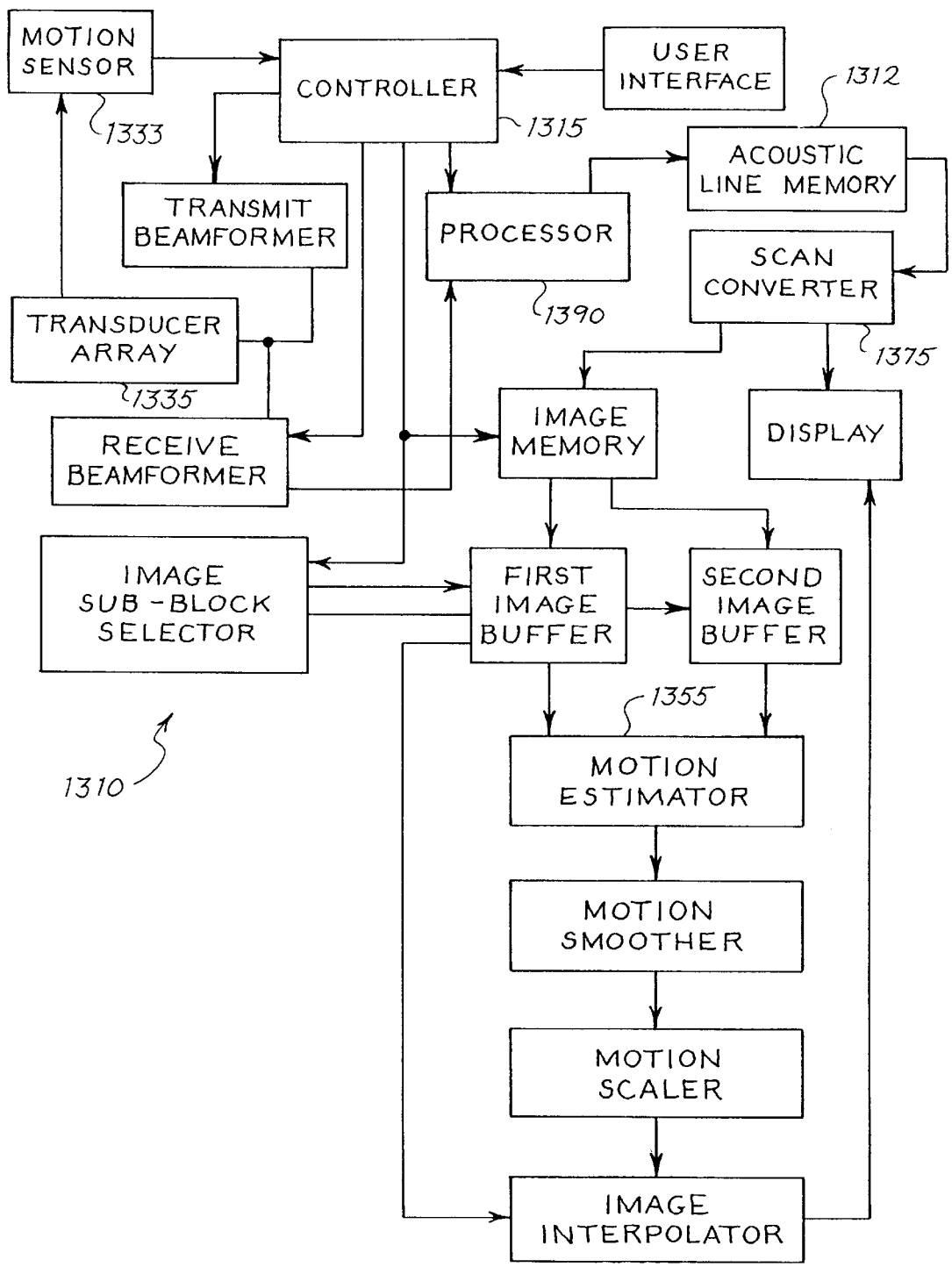
FIG. 13 is a block diagram of an ultrasound imaging system of another preferred embodiment.

FIG. 13 is a block diagram of an ultrasound imaging system 1310. This system 1310 is configured similarly to that of the system 1110 in the Adaptive Motion-Sensing Embodiments section. This system 1310 additionally comprises an acoustic line memory 1312 responsive to the controller 1315 and coupled to the scan converter 1375. The controller 1315 comprises means for generating a distortion-corrected image inside a region of interest in response to measured image or transducer motion. Specifically, the controller 1315 comprises means for reprocessing line data with corrected line spacing and means for repositioning sub-blocks of pixels in response to detected transducer or image motion. These functions, which can be performed in real time, are described below and in reference to FIG. 14.

Figure 14:
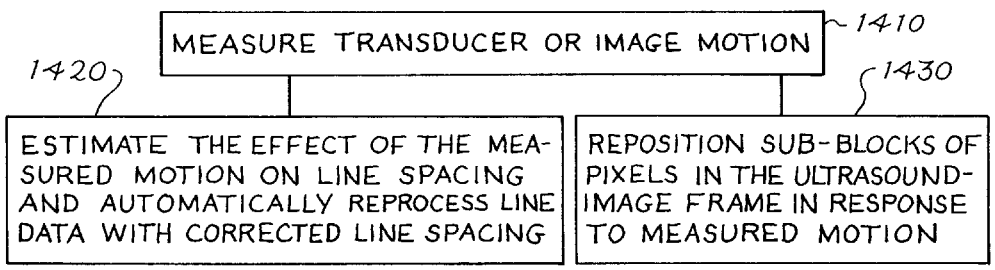
FIG. 14 is a flow chart of a method for generating a distortion-corrected image inside a region of interest in response to measured image or transducer motion.

FIG. 14 is a flow chart of a method for generating a distortion-corrected image inside a region of interest in response to measured image or transducer motion. First, transducer or image motion is measured (step 1410). In response to the measured motion, the controller 1315 can estimate the effect of the measured motion on line spacing and automatically reprocess line data with corrected line spacing (step 1420). Additionally, the controller 1315 can reposition sub-blocks of pixels in the ultrasound-image frame in response to measured motion (step 1430).

As shown in FIG. 14, first transducer or image motion is measured (step 1410). As described in the above-preferred embodiments, it is preferred that the motion estimator 1355 measure motion of a sub-block of pixels between two ultrasound-image frames in a region of interest. As described in the first two preferred embodiments above, a region of interest can comprise all or part of the frame and can be manually or automatically selected. Additionally, more than one region of interest can be selected. Alternatively, transducer motion can also be measured by a motion sensor 1333 in the housing of the transducer array 1335. The motion sensor 1333 can be an accelerometer or a magnetic position sensor, such as a "Flock of Birds" magnetic position sensor from Ascension Technology Corporation (Burlington, Vt.).

Next, in response to the measured motion, the controller 1315 can estimate the effect of the measured motion on line spacing and automatically reprocess line data with corrected line spacing (step 1420). For example, suppose that an ultrasound image frame is comprised of 100 lines and that the lines are physically spaced 0.5 mm apart on the surface of the transducer array 1335. The width of the image frame is, therefore, 50 mm. Also suppose that a single image frame takes 0.25 seconds to acquire and that the detected transducer motion is 4 lines (i.e., 2 mm) to the right between successive frames. As a result of this motion, the controller 1315 estimates that the right-most fired scan line will correspond to a location that is 2 mm outside of the image frame. The resulting image frame is distorted in the sense that 2 mm of information are not displayed in the 50 mm-wide image frame.

To compensate for this distortion, the display width of the image frame must be expanded by 2 mm and the line data (which is stored in the acoustic line memory 1312) must be reprocessed accordingly. To accomplish the reprocessing, the controller 1315 reprocesses the line data in the scan converter 1375 by changing the line spacing of the acoustic lines from 0.5 mm to 0.52 mm. A similar process can be applied to distortions in the depth direction. The scan-converted, distortion-corrected image can then be displayed.

Figure 15:
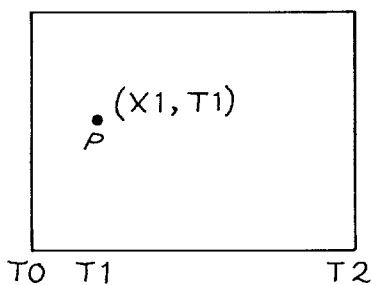
FIG. 15 is an illustration of an ultrasound image frame in which sub-block P is located at position X1.
Figure 16:
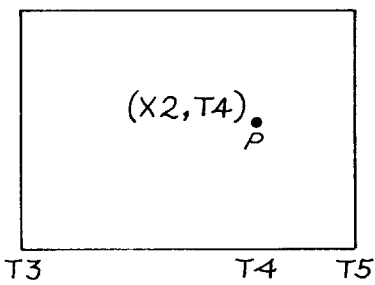
FIG. 16 is an illustration of an ultrasound image frame in which sub-block P is located at position X2.

Another type of image motion-related distortion is caused by time delay between lines acquired on the left and right hand side of the image frame. The controller 1315 can automatically reposition sub-blocks of pixels in the ultrasound-image frame (step 1430). As an example, suppose sub-block P (which in this example is a single pixel) is located at position X1 in the first acquired frame (FIG. 15) and at position X2 in the second acquired frame (FIG. 16). By a scan line's lateral position, the controller 1315 can calculate when pixels were acquired in a frame. In this example, in the first acquired frame, the left-most scan line was acquired at time T0, sub-block P was acquired at time T1, and the right-most scan line was acquired at time T2. In the second acquired frame, the left-most scan line was acquired at time T3, sub-block P was acquired at time T4, and the right-most scan line was acquired at time T5.

Because sub-block P is moving in this example, its location at time T2 will be different from its location at time T1. Accordingly, if a scan-converted image is displayed at time T2 without taking into account sub-block P's movement, the displayed image will contain inaccurate information regarding sub-block P's position.

To correct for this distortion, the velocity of sub-block P is calculated based on the time that the system 1310 acquires the scan line that captured sub-block P, not on the time that the system acquired the right-most scan line. Thus, the velocity of sub-block P would be $(X2-X1)/(T4-T1)$. Accordingly, the position of sub-block P at a time when the last scan line of the frame is acquired (i.e., T2) would be $X1+[(X2-X1)/(T4-T1)]*[T2-T1]$. With this information, the controller 1315 instructs the scan converter 1375 to reposition sub-block P and display a corrected frame rather than the originally acquired, distorted frame.

When the previous image frame was corrected using this method, it can be used as the basis for the next calculation, thereby producing an undistorted sequence of images.

Additionally, this method can be used with the methods of the Motion Compensation Embodiments section to provide a more exact calculation of a sub-block location in a motion-compensated interpolated frame. In the methods of the Motion Compensation Embodiments section, it can be assumed for simplicity that all pixels in the real frames were acquired at the time that the right-most scan line was acquired. With this assumption, in a motion-compensated interpolated frame generated between the frames of FIGS. 15 and 16, the velocity of sub-block P would be $(X2-X1)/(T5-T2)$. If one interpolated frame were generated at a time half-way between the times that the right-most lines of the two frames were acquired, the position of sub-block P in the interpolated frame would be $X1+[(X2-X1)/(T5-T2)]*[(T5-T2)/2]$, or $(X2+X1)/2$. If sub-block P or the transducer moved during the time the frame was scanned, this calculated position of sub-block P would result in a distorted interpolated frame, as described above.

The method of this preferred embodiment can correct for this distortion. That is, the velocity of sub-block P can be based on the times when the scan lines acquired sub-block P (i.e., times T1 and T4, not times T2 and T5). Accordingly, the position of sub-block P in the interpolated frame would be $X1+[(X2-X1)/(T4-T1)]*[(T5-T2)/2]$.

MOTION ESTIMATION

In the preferred embodiments described above, transducer or image motion is measured. The general field of motion measurement between successive image frames has been discussed widely in the public literature (see *Image Sequence Analysis*, T. S. Huang (Editor) Springer-Verlag, 1981 and "Interframe Interpolation of Cinematic Sequences," Ribas-Corbera & Sklansky, Journal of Visual Communication and Image Representation, Vol. 4, No. 4, December 1993 (pages 392–46)). While any means of motion measurement can be used, it is presently preferred that a motion estimator employing a Moving-Picture-Experts-Group (MPEG) standard be used to track the movement of a block of pixels between image frames. While MPEG applies to both video and audio, only video (specifically, the luminance component) is relevant here. It is preferred that a L64720A motion estimator from LSI Logic be used.

An MPEG motion estimator calculates, in real time, motion vectors for a blocks of pixels moving from one image frame to the next. It is preferred that the ultrasound image be split into 32×32 or 16×16 macroblocks. Between successive input frames, a best fitting motion estimation is made for each block, preferably using a sum of absolute differences in pixel intensity. Other techniques can also be used. An error between the two blocks corresponding to the degree of correlation can also be calculated. The vector shifts and error components are then coded for transfer.

With the motion vectors, the ultrasound system can generate an interpolated frame from: (a) forward prediction from the earlier frame, (b) backward prediction from the later image, or (c) a combination of the forward and backward predictions. If a motion estimate is questionable (i.e., the calculated error is large), it can be replaced with a mean of surrounding low-error estimates. Alternatively the matrix of vector estimates may be low-pass or median filtered. Other filtering operations, including non-linear filtering, can also be used. In the case of a translational motion, it is known that all estimates of motion should be similar and therefore a high degree of low-pass filtering is permissible without interfering with image quality.

To obtain a smoother image-motion effect, the ultrasound system can interpolate intermediate displacement vectors. For example, if the ultrasound system computes motion estimates for each of the 16×16 blocks of pixels in the image frame, it can generate interpolated displacement vectors to effectively cover the image frame with 8×8 blocks of pixels. This process may be repeated with smaller blocks (4×4, etc.) to obtain a smoother motion effect. Notice that larger blocks are preferred because they will generally be more stable and accurate. Also, larger blocks can tolerate larger pixel displacements. Since processing large blocks is computationally expensive, multiple processors can be used. Specifically, the TMS320C80 circuit from Texas Instruments allows for parallel processing.

If image motions are very large or computational complexities impose limitations on maximum block size, the original image data can be down sampled in order to increase real pixel spacing. For example, pixel sub-blocks can be averaged and replaced by single values. Other methods, preferably ones in which a low-pass filter is used prior to down sampling, can be used and are well known in the art. Additionally, pixel value resolution can be compressed to lessen computation complexity.

Similarly, the output-pixel-value-to-input-signal-level mapping can be altered to give more reliable motion estimates. For example, if the region is mostly white (i.e., it requires high pixel values), it may be preferable to lower the mean pixel value and disperse it over the available range (e.g., if the pixel range is 128–255, it may be remapped to 0–255 with increments of 2 by subtracting 128 from the original values and doubling for more effective use of the available computational resource).

As a result of motion-compensated interpolation, the interpolated image may contain artifacts. Because interpolated images are presented in a moving sequence of frames, small, individual artifacts may not be very noticeable. Regularly occurring or large, blocky artifacts may be discernible, however. To remove such artifacts, a low-pass filter can be applied to the entire interpolated image or in regions of the block boundaries, e.g., +/–four pixels from the boundary. A spatial two-dimensional low-pass filter applied to the image may be non-symmetric. Since axial resolution is generally better than lateral resolution, the low-pass cutoff frequency in the lateral (width) direction may be lower than in the axial (depth) direction.

Another way to remove artifacts is by offsetting the centers of the blocks that cover the image frame in random directions to reduce the likelihood of a regular block structure being evident. With such an approach, it is important to avoid holes by ensuring that the entire image frame is covered. The centers can also be offset so that the blocks overlap (e.g., 16×16 blocks spaced at 12 pixel spacing). Where blocks overlap, the pixel output level is preferably given by the mean of the contributing pixel values.

Additionally, because artifacts are more noticeable in a freeze frame or slow motion replay mode, the ultrasound system can be modified to present only real images in these modes.

As mentioned above, using a motion estimator employing an MPEG standard is merely one may in which motion can be measured. One skilled in the art can derive several enhancements including, for example, using gradient or differential techniques (see *Image Sequence Analysis* by Huang), using optical flow based methods (see "Restoration of the Velocity Field of the Heart from Two-Dimensional Echocardograms" by Mailloux et al., IEEE Transactions on Medical Imaging, Vol. 8, No. 2, June 1989 (pages 143–153)), and using the well-known technique of sub-pixel resolution motion tracking. See also "A Locally Quadratic Model of the Motion Estimation Error Criterion Function and Its Application to Subpixel Interpolation," Li and Gonzales, IEEE Transactions on Circuits and Systems for Video Technology, Vol. 6, No. 1. Page 188, February 1996.

One skilled in the art can also derive alternative means of detecting motion. A general purpose, high-powered digital-signal-processor integrated circuit can be programmed with high-level code to perform both MPEG compression and decompression. It is preferred that a TMS320C80 MVP circuit and high-level code, both available from Texas Instruments, be used. One skilled in the art would be able to adapt the code to implement the functions described in the above preferred embodiments. Because they are less specialized than circuits employing the MPEG standard, modified general-purpose circuits have the disadvantage of being less efficient than MPEG motion processors.

It is preferred to perform motion estimates on a scan-converted, rectangular acoustic grid. With such a grid, each pixel has only a limited but necessary level of detail (e.g., 8 bits). If the level of detail is too great (e.g., 16 or 24 bits) or if the pixel density of the output display device (which contains multiple pixels per acoustic grid) is used, computations become more complex.

In addition to scan-converted, rectangular acoustic grids, motion estimates can be applied to RF (raw acoustic line) data. In this context raw acoustic line data means any of true RF, IF, or baseband In phase/Quadrature data. Motion estimates on RF data for blood speckle tracking are known in the art (see "A Novel Method for Angle Independent Ultrasonic Imaging of Blood Flow and Tissue Motion," L. N. Bohs, IEEE Trans, BME Vol. 38, No. 3, March 1991, pp. 280–286). If RF data frames are used to produce an interpolated "raw acoustic line data frame," distortions due to the fact that the lines are not in a rectangular format may cause only minor problems. However, it should be noted that in the case of sector- or Vector®-type format, motions appear to be larger at the top than at the bottom due to the high line density at the top of the image. For example, for a given azimuthal translation, five lines are crossed at the top of the image, while only three lines are crossed at the bottom of the image. Accordingly, if the RF image data is motion estimated, it is preferred that the data is sampled at least twice per RF period.

It is important to note that the various features described in the above embodiments can be used alone or in various sub-combinations with one another. It is also important to note that the foregoing detailed description is merely an illustration of selected forms that the invention can take and not as a definition of the invention. It is only the following claims, including all equivalents, that are intended to define the scope of this invention.

What is claimed is:

1. A method for correcting distortion of image pixels due to a line acquisition time delay in an ultrasound image in response to measured image or transducer motion, the method comprising:

(a) measuring motion; and then
   (b) correcting distortion in an ultrasound image in response to the measured motion by repositioning at least one sub-block of said pixels in response to motion measured in (a).

2. The method of claim 1, wherein (a) comprises measuring motion with a motion sensor in a transducer.

3. The method of claim 1, wherein (a) comprises measuring motion by measuring motion of a sub-block of pixels between at least two ultrasound images.

4. The method of claim 1, wherein (b) comprises correcting distortion in the entire ultrasound image.

5. The method of claim 1, wherein (b) comprises correcting distortion in a portion of the ultrasound image.

6. The method of claim 1, wherein the method further comprises manually selecting a region of interest in the ultrasound image and wherein (b) comprises correcting distortion in the region of interest.

7. The method of claim 1, wherein the method further comprises automatically selecting a region of interest in the ultrasound image and wherein (b) comprises correcting distortion in the region of interest.

8. A method for generating a distortion-corrected ultrasound image in response to measured image or transducer motion, the distortion of image pixels in the ultrasound image due to a line acquisition time delay, the method comprising:

(a) measuring motion; and then
   (b) generating a distortion-corrected ultrasound image in response to the measured motion by repositioning at least one sub-block of said pixels in response to motion measured in (a).

9. The method of claim 8, wherein (a) comprises measuring motion with a motion sensor in a transducer.

10. The method of claim 8, wherein (a) comprises measuring motion by measuring motion of a sub-block of pixels between at least two ultrasound images.

11. The method of claim 8, wherein (b) comprises generating a distortion-corrected image in the entire ultrasound image.

12. The method of claim 8, wherein (b) comprises generating a distortion-corrected image in a portion of the ultrasound image.

13. The method of claim 8, wherein the method further comprises manually selecting a region of interest in the ultrasound image and wherein (b) comprises generating a distortion-corrected image in the region of interest.

14. The method of claim 8, wherein the method further comprises automatically selecting a region of interest in the ultrasound image and wherein (b) comprises generating a distortion-corrected image in the region of interest.

15. A method for correcting distortion in an ultrasound image in response to measured image or transducer motion, the method comprising:

(a) measuring motion; and then (b) correcting distortion in an ultrasound image in response to the measured motion by estimating an effect of the measured motion on line spacing and expanding a display width of the ultrasound image in response to motion measured in (a).

16. The method of claim 15, wherein (a) comprises measuring motion with a motion sensor in a transducer.

17. The method of claim 15, wherein (a) comprises measuring motion by measuring motion of a sub-block of pixels between at least two ultrasound images.

18. The method of claim 15, wherein (b) comprises correcting distortion in the entire ultrasound image.

19. The method of claim 15, wherein (b) comprises correcting distortion in a portion of the ultrasound image.

20. The method of claim 15, wherein the method further comprises manually selecting a region of interest in the ultrasound image and wherein (b) comprises correcting distortion in the region of interest.

21. The method of claim 15, wherein the method further comprises automatically selecting a region of interest in the ultrasound image and wherein (b) comprises correcting distortion in the region of interest.

22. A method for generating a distortion-corrected ultrasound image in response to measured image or transducer motion, the method comprising:

(a) measuring motion; and then (b) generating a distortion-corrected ultrasound image in response to the measured motion by estimating an effect of the measured motion on line spacing and expanding a display width of the ultrasound image in response to motion measured in (a).

23. The method of claim 22, wherein (a) comprises measuring motion with a motion sensor in a transducer.

24. The method of claim 22, wherein (a) comprises measuring motion by measuring motion of a sub-block of pixels between at least two ultrasound images.

25. The method of claim 22, wherein (b) comprises generating a distortion-corrected image in the entire ultrasound image.

26. The method of claim 22, wherein (b) comprises generating a distortion-corrected image in a portion of the ultrasound image.

27. The method of claim 22, wherein the method further comprises manually selecting a region of interest in the ultrasound image and wherein (b) comprises generating a distortion-corrected image in the region of interest.

28. The method of claim 22, wherein the method further comprises automatically selecting a region of interest in the ultrasound image and wherein (b) comprises generating a distortion-corrected image in the region of interest.

* * * * *

UNITED STATES PATENT AND TRADEMARK OFFICE
CERTIFICATE OF CORRECTION

PATENT NO.   : 6,083,168
DATED        : July 4, 2000
INVENTOR(S)  : John A. Hossack et al.

It is certified that error appears in the above-identified patent and that said Letters Patent is hereby corrected as shown below:

Title Page

Column 1,
Item [63] delete "5,878,830" and substitute -- 5,873,830 -- in its place.

Column 8,
Line 16, delete "input. signal" and substitute -- input signal -- in its place.
Line 29, delete "filer" and substitute -- filter -- in its place.
Line 44, delete "As-used" and substitute -- As used -- in its place.

Column 9,
Line 57, delete "motion is present," and substitute -- motion present, -- in its place.
Line 62, delete "estimates employed" and substitute -- estimates are emplyed -- in its place.

Column 10,
Line 1, delete "(i" and substitute -- (i. -- in its place.
Line 30, delete "α (n-1)" and substitute -- O (n-1) -- in its place.

Column 11,
Line 10, second line of equation (in the denominator), delete
"(I (n,x,y) - O (n - 1,x,y) )$^2$" and substitute -- (I (n,x,y) + O (n - 1,x,y) )$^2$ -- in its place.
Line 51, delete "sum-of-absolute-differences -- in its place.

Column 14,
Line 66, delete "in measured" and substitute -- is measured -- in its place.

Column 17,
Line 53, delete "varying" and substitute -- vary -- in its place.

Column 19,
Line 14, delete "115" and substitute -- 1115 -- in its place.
Line 19, delete "fill" and substitute -- full -- in its place.
Line 29, delete "ensuring that image repeated" and substitute -- ensuring that images repeatedly -- in its place.

UNITED STATES PATENT AND TRADEMARK OFFICE
CERTIFICATE OF CORRECTION

PATENT NO. : 6,083,168
DATED : July 4, 2000
INVENTOR(S) : John A. Hossack et al.

It is certified that error appears in the above-identified patent and that said Letters Patent is hereby corrected as shown below:

Column 21,
Line 65, delete "a blocks" and substitute -- a block -- in its place.

Column 23,
Line 13, delete "may" and substitute -- way -- in its place.

Signed and Sealed this

Twenty-first Day of August, 2001

*Attest:*

*Attesting Officer*

NICHOLAS P. GODICI
*Acting Director of the United States Patent and Trademark Office*